United States Patent [19]
Sato et al.

[11] Patent Number: 6,037,341
[45] Date of Patent: *Mar. 14, 2000

[54] CARBAPENEM DERIVATIVES

[75] Inventors: Nobuaki Sato; Manabu Sasho; Atsushi Kamata; Takaaki Suzuki; Isao Sugiyama; Kanemasa Katsu; Takeshi Suzuki, all of Ibaraki, Japan

[73] Assignee: Eisai Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/765,387
[22] PCT Filed: Jun. 29, 1995
[86] PCT No.: PCT/JP95/01233
§ 371 Date: Dec. 18, 1996
§ 102(e) Date: Dec. 18, 1996
[87] PCT Pub. No.: WO96/01261
PCT Pub. Date: Jan. 18, 1996

[30] Foreign Application Priority Data

Jul. 6, 1994 [JP] Japan .................................. 6-154055
Jun. 8, 1995 [JP] Japan .................................. 7-141832

[51] Int. Cl.[7] .......................... C07D 477/20; C07D 7/18; A61K 31/40; A61K 31/445
[52] U.S. Cl. .......................... 514/210; 540/350; 540/200; 548/524; 548/406; 546/208; 546/14
[58] Field of Search ............................ 514/210; 540/350

[56] References Cited

U.S. PATENT DOCUMENTS

| | | | |
|---|---|---|---|
| 4,822,787 | 4/1989 | Murata et al. | 514/210 |
| 4,925,838 | 5/1990 | Murata et al. | 514/210 |
| 4,963,544 | 10/1990 | Murata et al. | 514/210 |
| 5,438,054 | 8/1995 | Nakagawa et al. | 514/210 |
| 5,550,121 | 8/1996 | Nakagawa | 540/350 |

FOREIGN PATENT DOCUMENTS

| | | |
|---|---|---|
| 51-73191 | 6/1976 | Japan . |
| 63-179876 | 7/1988 | Japan . |
| 2-1491 | 1/1990 | Japan . |
| 2-15080 | 1/1990 | Japan . |
| 4-321688 | 11/1990 | Japan . |
| 4-321688 | 11/1992 | Japan . |
| 5-339269 | 12/1993 | Japan . |
| 6-16671 | 1/1994 | Japan . |
| 6-1791 | 1/1994 | Japan . |
| 6-87858 | 3/1994 | Japan . |
| 6-157544 | 6/1994 | Japan . |
| 7-291973 | 11/1995 | Japan . |

Primary Examiner—Mark L. Berch
Attorney, Agent, or Firm—Flynn, Thiel, Boutell & Tanis, P.C.

[57] ABSTRACT

Compounds having potent antimicrobial effects over Gram-positive bacteria and Gram-negative bacteria, a high stability to β-lactamases and DHP-I and a high safety for the human body and a process for producing the same. Carbapenem compounds represented by the following general formula (I) or salts thereof:

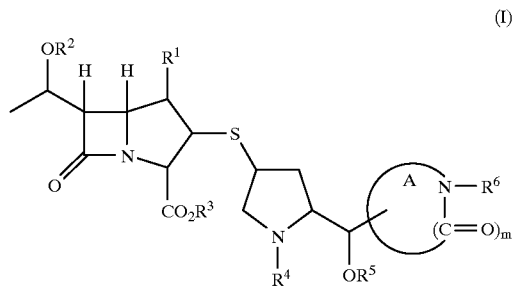

wherein the ring A represents a 3- to 7-membered non-aromatic ring containing at least one nitrogen atom and optionally having a substituent other than $R^6$; $R^1$ represents hydrogen or methyl; $R^2$ and $R^5$ are the same or different and each represents hydrogen or a protecting group of the hydroxyl group; $R^3$ represents hydrogen or a protecting group of the carboxyl group; $R^4$ represents hydrogen, lower alkyl or a protecting group of the amino group; $R^6$ represents: (1) hydrogen, (2) lower alkyl, optionally substituted by an optionally protected hydroxy, carbamoyl, formimidoyl, acetimidoyl or

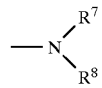

wherein $R^7$ and $R^8$ are the same or different
and each represents hydrogen, lower alkyl, or a protecting group of the amino group), or (3) a protecting group of the amino group or a protecting group of the imino group; and m is 0 or 1. These compounds have antimicrobial effects and are useful as a drug.

14 Claims, No Drawings

CARBAPENEM DERIVATIVES

This application is a 371 of PCT/US95/01299 filed Jun. 29, 1995.

FIELD OF THE INVENTION

This invention relates to novel carbapenem derivatives or salts thereof and a process for producing the same.

BACKGROUND OF THE INVENTION AND PRIOR ART

Since thienamycins were found in 1976 (JP-A 51-73191 (1976)), there have been made a number of researches and developments on carbapenem antibiotics.

Even today, studies are under way to synthesize a number of carbapenem compounds which have potent and broad antimicrobial spectra over Gram-negative bacteria and Gram-positive bacteria and are highly stable to many $\beta$-lactamases.

For example, Taura et al. (JP-A 6-157544(1994)) have reported carbapenem compounds having a $\beta$-configuration methyl group, a (6,7-dihydro-5H-pyrazolo[1,2-$\alpha$] [1,2,4] triazolium-6-yl)] thio group and a 1-substituted-hydroxyethyl group respectively at the 1-, 2- and 6-positions of the carbapenem skeleton. In addition, a number of compounds have been reported by JP-A 6-1791(1994), JP-A 6-16671(1994), JP-A 5-339269(1993), etc.

JP-A 6-87858(1994) has disclosed carbapenem derivatives having an aminoalkylpyrrolidinylthio group at the 2-position of the carbapenem skeleton and being similar to the compounds of the present invention in structure. This patent generally indicates carbapenem compounds having a 2-substituted-pyrrolidin-4-ylthio group as the side chain at the 2-position of the carbapenem skeleton wherein the substituent is a branched alkylene group having a primary, secondary or tertiary amino group or an ammonio group at the terminus. However, it neither states in general nor suggests any compound which has a cyclic amine- or lactam-substituted hydroxymethyl group as the side chain of the pyrrolidinylthio group at the 2-position of the carbapenem skeleton.

Frequent use of penicillin and cephalosporin antibiotics having broad antimicrobial spectra has caused a social problem of the appearance of resistant bacteria, in particular, methicillin-resistant *Staphylococcus aureus* (MRSA) and resistant *Pseudomonas aeruginosa*. There has been known no drug efficacious against these resistant bacteria and thus it is urgently required to develop novel chemicals therefor.

As described above, carbapenem antibiotics have potent and broad antimicrobial spectra over Gram-negative and Gram-positive bacteria and are stable to $\beta$-lactamases. Although these carbapenem antibiotics are efficacious against bacteria resistant to a number of penicillin and cephalosporin antibiotics, their antimicrobial activities on these resistant bacteria are not always sufficient. The carbapenem antibiotics are poor in chemical stability and, furthermore, very easily metabolized by dehydropeptidase-I (DHP-I) localized in the kidney, etc., and thus lose their antimicrobial activities within a short period of time in vivo. These properties make the compounds not necessarily useful as a drug.

In addition, there remain some problems regarding safety for the human body (for example, side effects on the central nervous system and nephrotoxicity due to decomposition products) and an increase in resistant bacteria caused by the frequent use of carbapenem antibiotics such as thienamycin and imipenem.

Although several carbapenem antibiotics are now employed in the treatment of infectious diseases, there has not been developed a carbapenem antibiotic which has an excellent antimicrobial effect and a broad antimicrobial spectrum and is satisfactory in stability in vivo, safety for the human body (i.e., avoiding any toxicity), etc.

DISCLOSURE OF THE INVENTION

The present inventors have conducted extensive studies on the synthesis of carbapenem derivatives in order to solve the above-mentioned problems and consequently found out that compounds represented by the following general formula (I), which have 2-substituted pyrrolidinylthio groups having various substituents at the 2-position, are useful as drugs because of their potent antimicrobial activities and high safety for the human body, thus completing the present invention.

Accordingly, the present invention relates to novel carbapenem derivatives represented by the following general formula (I) and being useful as antimicrobial agents, or salts thereof, and a process for producing the same:

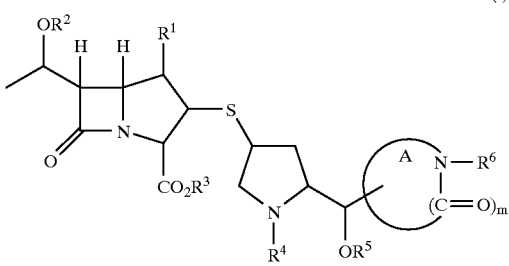

wherein the ring A represents a 3- to 7-membered ring containing at least one nitrogen atom and optionally having a substituent other than $R^6$; $R^1$ represents hydrogen or methyl; $R^2$ and $R^5$ are the same or different and each represents hydrogen or a protecting group of the hydroxyl group; $R^3$ represents hydrogen or a protecting group of the carboxyl group; $R^4$ represents hydrogen, lower alkyl or a protecting group of the amino group; $R^6$ represents: (1) hydrogen, (2) lower alkyl optionally substituted by optionally protected hydroxy, carbamoyl, formimidoyl, acetimidoyl or

(wherein $R^7$ and $R^8$ are the same or different
and each represents hydrogen, lower alkyl, or a protecting group of the amino group), or (3) a protecting group of the amino group or a protecting group of the imino group; and m is 0 or 1.

The present invention further provides an antimicrobial agent comprising as the active ingredient the above-mentioned compound or a pharmacologically acceptable salt thereof; the use of the above-mentioned compound or salt thereof for producing an antimicrobial agent; a method for preventing or treating microbisms which comprises administering a pharmacologically efficacious dose of the above-mentioned compound, or salt thereof, to a patient; and a medicinal composition which comprises a pharmacologically efficacious amount of the above-mentioned compound, or salt thereof, and pharmacologically acceptable carrier(s).

Now, the contents of the present invention and the terms, etc., used herein will be described in detail.

First, the compounds of the present invention include optical isomers and stereoisomers on the basis of asymmetric carbon atoms at the 1-, 5-, 6- and 8-positions of the carbapenem skeleton, as shown in the following formula:

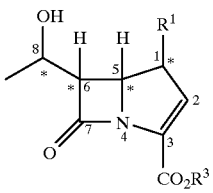

wherein $R^1$ represents hydrogen or methyl; and * represents an asymmetric carbon atom. Although these isomers are all represented by a single formula for the sake of convenience, the present invention is not restricted to the formula given for the sake of convenience but involves all of the isomers and isomer mixtures on the basis of each of these asymmetric carbons.

Further, there are isomers on the basis of the asymmetric carbon atom in the substituent on the side chain at the 2-position of the carbapenem skeleton. The present invention involves all of these optical isomers and stereoisomers too.

From the viewpoint of antimicrobial effect, however, the compounds represented by the following formula, or salts thereof, are preferable:

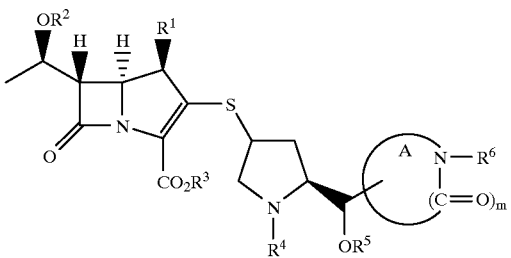

(II)

wherein the ring A represents a 3- to 7-membered ring containing at least one nitrogen atom and optionally having a substituent other than $R^6$; $R^1$ represents hydrogen or methyl; $R^2$ and $R^5$ are the same or different and each represents hydrogen or a protecting group of the hydroxyl group; $R^3$ represents hydrogen or a protecting group of the carboxyl group; $R^4$ represents hydrogen, lower alkyl or a protecting group of the amino group; $R^6$ represents: (1) hydrogen, (2) lower alkyl optionally substituted by optionally protected hydroxy, carbamoyl, formimidoyl, acetimidoyl or

(wherein $R^7$ and $R^8$ are the same or different and each represents hydrogen, lower alkyl, or a protecting group of the amino group), or (3) a protecting group of the amino group or a protecting group of the imino group; and m is 0 or 1.

$R^1$ represents a hydrogen atom or a methyl group and methyl is preferably used therefor.

$R^2$ and $R^5$ are the same or different and each represents a hydrogen atom or a protecting group of the hydroxyl group. The protecting group of the hydroxyl group may be an arbitrary one without restriction, so long as it is a group commonly known as a protecting group of a hydroxyl group in organic syntheses. Particular examples thereof include lower alkylsilyl groups such as trimethylsilyl and t-butyldimethyl-silyl groups; lower alkoxymethyl groups such as methoxymethyl and 2-methoxyethoxymethyl groups; a tetrahydropyranyl group and the like; aralkyl groups such as benzyl, p-methoxybenzyl, 2,4-dimethoxybenzyl, o-nitrobenzyl, p-nitrobenzyl and trityl groups; acyl groups such as formyl and acetyl groups; lower alkoxycarbonyl groups such as t-butoxycarbonyl, 2-iodoethoxy-carbonyl and 2,2,2-trichloroethoxycarbonyl groups; alkenyloxy-carbonyl groups such as 2-propenyloxycarbonyl, 2-chloro-2-propenyloxycarbonyl, 3-methoxycarbonyl-2-propenyloxycarbonyl, 2-methyl-2-propenyloxycarbonyl, 2-butenyloxycarbonyl and cinnamyloxycarbonyl groups; and aralkyloxycarbonyl groups such as benzyloxycarbonyl, p-methoxybenzyloxycarbonyl, o-nitro-benzyloxycarbonyl and p-nitrobenzyloxycarbonyl groups.

$R^3$ represents a hydrogen atom or a protecting group of the carboxyl group.

The protecting group of the carboxyl group may be an arbitrary one without restriction, so long as it is a group commonly known as a protecting group of a carboxyl group in organic syntheses. Particular examples thereof include linear and branched lower alkyl groups having 1 to 4 carbon atoms such as methyl, ethyl, isopropyl and t-butyl groups; halogenated lower alkyl groups such as 2-iodoethyl and 2,2,2-trichloro-ethyl groups; lower alkoxymethyl groups such as methoxymethyl, ethoxymethyl and isobutoxymethyl groups; lower aliphatic acyloxymethyl groups such as butyryloxymethyl and pivaloyloxy-methyl groups; 1-(lower alkoxy)carbonyloxyethyl groups such as 1-methoxycarbonyloxyethyl and 1-ethoxycarbonyloxy-ethyl groups; aralkyl groups such as benzyl, p-methoxybenzyl, o-nitrobenzyl and p-nitrobenzyl groups; a benzhydryl group and a phthalidyl group.

$R^4$ represents a hydrogen atom, a lower alkyl group or a protecting group of the amino group.

The lower alkyl group means a linear or branched alkyl group having 1 to 6 carbon atoms such as methyl, ethyl, n-propyl, i-propyl, n-butyl, i-butyl, sec-butyl, t-butyl, n-pentyl, i-pentyl, sec-pentyl, t-pentyl, neopentyl, 1-methylbutyl, 2-methylbutyl, 1,1-dimethylpropyl, 1,2-dimethylpropyl, n-hexyl, i-hexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl groups.

The protecting group of the amino group may be an arbitrary one without restriction, so long as it is a group commonly known as a protecting group of an amino group in organic syntheses. Particular examples thereof include optionally substituted lower alkanoyl groups such as formyl, acetyl, chloroacetyl, dichloroacetyl, propionyl, phenylacetyl, phenoxyacetyl and thienylacetyl groups; optionally substituted lower alkoxycarbonyl groups such as benzyloxycarbonyl, t-butoxycarbonyl and p-nitrobenzyloxycarbonyl groups; substituted lower alkyl groups such as methyl, t-butyl, 2,2,2-trichloroethyl, trityl, p-methoxybenzyl, p-nitrobenzyl, diphenylmethyl and pivaloyloxymethyl groups; substituted silyl groups such as trimethylsilyl and t-butyldimethylsilyl groups; and optionally substituted benzylidene groups such as benzylidene, salicylidene, p-nitrobenzylidene, m-chlorobenzylidene, 3,5-di(t-butyl)-4-hydroxybenzylidene and 3,5-di(t-butyl)benzylidene groups.

Such a protecting group can be eliminated by any conventional method such as hydrolysis or reduction depending on the type thereof.

$R^6$ represents: (1) a hydrogen atom, (2) a lower alkyl group optionally substituted by optionally protected hydroxyl, carbamoyl, formimidoyl, acetimidoyl or

(wherein $R^7$ and $R^8$ are the same or different and each represents a hydrogen atom, a lower alkyl group or a protecting group of the amino group), or (3) a protecting group of the amino group or a protecting group of the imino group.

As the examples of the protecting group of the hydroxyl group in the optionally protected hydroxyl group, citation can be made of the protecting groups of a hydroxyl group described above.

The lower alkyl group and the protecting group of the amino group in $R^7$ and $R^8$ are each the same as those defined above.

The protecting group of the amino group or the protecting group of the imino group in $R^6$ may be an arbitrary one without restriction, so long as it is a group commonly known as a protecting group of an amino group or a protecting group of an imino group in organic syntheses. Particular examples thereof include optionally substituted lower alkanoyl groups such as formyl, acetyl, chloroacetyl, dichloroacetyl, propionyl, phenylacetyl, phenoxyacetyl and thienylacetyl groups; optionally substituted lower alkoxy-carbonyl groups such as benzyloxycarbonyl, t-butoxycarbonyl and p-nitrobenzyloxy-carbonyl groups; substituted lower alkyl groups such as methyl, t-butyl, 2,2,2-trichloroethyl, trityl, p-methoxy-benzyl, p-nitrobenzyl, diphenylmethyl and pivaloyloxymethyl groups; substituted silyl groups such as trimethyl-silyl and t-butyldimethylsilyl groups; and optionally substituted benzylidine groups such as benzylidene, salicylidene, p-nitrobenzylidene, m-chlorobenzylidene, 3,5-di(t-butyl)-4-hydroxybenzylidene and 3,5-di(t-butyl)benzylidene groups.

Such a protecting group can be eliminated by any conventional method such as hydrolysis or reduction depending on the type of the protecting group.

Accordingly, particular examples of $R^6$ include, in addition to the hydrogen atom, lower alkyl groups substituted by optionally protected hydroxyl groups such as hydroxymethyl, hydroxyethyl, hydroxypropyl and hydroxybutyl groups; lower alkyl groups substituted by carbamoyl groups such as carmaboylmethyl, carbamoylethyl, carbamoylpropyl and carbamoylbutyl groups; lower alkyl groups substituted by formimidoyl groups such as formimidoylmethyl, formimidoylethyl, formimidoylpropyl and formimidoylbutyl groups; lower alkyl groups substituted by acetimidoyl groups such as acetimdoylmethyl, acetimidoylethyl, acetimidoylpropyl and acetimidoylbutyl groups; substituted amino-lower alkyl groups such as aminomethyl, aminoethyl, aminopropyl, aminobutyl, N-methylaminomethyl, N-methylaminoethyl, N-methylaminopropyl, N-methylaminobutyl, N,N-dimethylaminomethyl, N,N-dimethylamino-ethyl, N,N-dimethylaminopropyl, N,N-dimethylaminobutyl, N,N-ethylmethylaminomethyl, N,N-ethylmethylaminoethyl, N,N-ethylmethylaminopropyl and N,N-ethylmethylaminobutyl groups; and the above-mentioned protecting groups of an amino group and the protecting groups of an imino group, though the present invention is not restricted thereto.

m is 0 or 1.

The type of the salt is not restricted and examples thereof include inorganic acid addition salts such as hydrochloride, sulfate, carbonate, bicarbonate, hydrobromide and hydriodide; organic carboxylic acid addition salts such as acetate, maleate, lactate, tartrate and trifluoroacetate; organic sulfonic acid addition salts such as methanesulfonate, hydroxymethanesulfonate, hydroxyethanesulfonate, benzenesulfonate, toluenesulfonate and taurine salt; amine addition salts such as trimethylamine salt, triethylamine salt, pyridine salt, procaine salt, picoline salt, dicyclohexylamine salt, N,N'-dibenzylethylenediamine salt, N-methyl-glucamine salt, diethanolamine salt, triethanolamine salt, tris(hydroxy-methylamino)methane salt and phenethylbenzylamine salt; alkali metal addition salts such as sodium salt and potassium salt; alkaline earth metal addition salts such as magnesium salt and calcium salt; and amino acid addition salts such as arginine salt, lysine salt, serine salt, glycine salt, aspartate and glutamate.

The term "pharmacologically acceptable salt" as used herein refers to the conventional ones commonly employed in the production of drugs.

The ester in the above general formula (I) refers to an ester at the carboxyl group at the 3-position of the carbapenem skeleton containing an ester group which is physiologically acceptable and hydrolyzable under physiological conditions. Examples thereof include $C_{1-6}$ alkyl, benzyl, 4-methoxybenzyl, alkanoyloxyalkyl (for example, acetoxymethyl, propionyloxymethyl and pivaloxymethyl), alkoxy-carbonyloxyalkyl (for example, methoxycarbonyloxymethyl, ethoxycarbonyloxymethyl and 2-methoxycarbonyloxyethyl) and 5-(methyl-2-oxy-1,3-dioxo-4-yl)-methyl groups.

The ring A represents a 3- to 7-membered ring containing at least one nitrogen atom and optionally having a substituent other than $R^6$.

Examples of the 3- to 7-membered ring containing at least one nitrogen atom include aziridine, azetidine, pyrrolidine, piperidine, homopiperidine, imidazolidine, pyrazolidine, piperazine, pyrroline, imidazoline and pyrazoline rings.

The expression "optionally having a substituent other than $R^6$" means optionally having one or more substituents, for example, a hydrogen atom, a hydroxyl group, a thiol group, halogen atoms, and nitrile, azido, alkyl, alkenyl, alkynyl, alkoxy, halogenoalkyl, guanidino, formimidoyl, acetimidoyl, carbamoyl, thiocarbamoyl, carbamoylalkyl, carbamido, alkanoyl, amino, alkylamino, dialkylamino, aminoalkyl carboxy, alkoxycarbonyl, alkoxycarbonylalkyl, aminoalkyl-aminoalkyl, alkylcarbonyloxy, ammonium, cycloalkyl, cycloalkenyl, phenyl, alkylthio, phenylthio, benzyl, benzoyl and halogenoaryl groups.

The present inventors have found out that carbapenem derivatives having, as the side chain of the pyrrolidinylthio group at the 2-position of the carbapenem skeleton, a group represented by the following general formula, have excellent antimicrobial activities, thus completing the present invention:

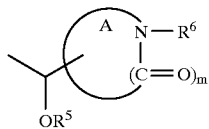

wherein the ring A represents a 3- to 7-membered ring containing at least one nitrogen atom and optionally having a substituent other than $R^6$; $R^5$ represents hydrogen or a protecting group of the hydroxyl group; $R^6$ represents: (1) hydrogen, (2) lower alkyl optionally substituted by optionally protected hydroxy, carbamoyl, formimidoyl, acetimidoyl or

(wherein $R^7$ and $R^8$ are the same or different and each represents hydrogen, lower alkyl, or a protecting group of the amino group), or (3) a protecting group of the amino group or a protecting group of the imino group; and m is 0 or 1.

The compounds of the present invention are characterized by having the structures where the pyrrolidinylthio group, which is the side chain at the 2-position of the carbapenem skeleton, has a cyclic amine- or lactam-substituted hydroxymethyl group at the 2-position of the pyrrolidine ring. Examples of the cyclic amine- or lactam-substituted hydroxymethyl group include aziridinylhydroxymethyl, azetidinylhydroxymethyl, pyrrolidinylhydroxymethyl, piperidinylhydroxymethyl, homopiperidinylhydroxymethl, 2-aziridinonylhydroxymethyl, 2-azetidinonylhydroxymethyl, 2-pyrrolidinonylhydroxymethyl, 2-piperidinonylhydroxymethyl and 2-homopiperidinonyl-hydroxy-methyl groups, each optionally having substituent (s) other than $R^6$.

Accordingly, preferable examples of the carbapenem derivatives of the present invention include the compound represented by the following formula, and salts and esters thereof:

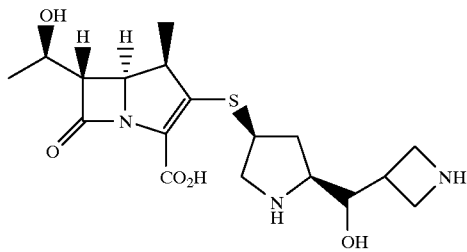

the compound represented by the following formula, and salts and esters thereof:

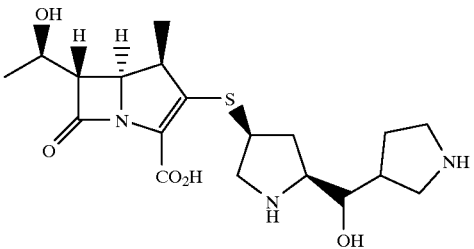

the compound represented by the following formula, and salts and esters thereof: and

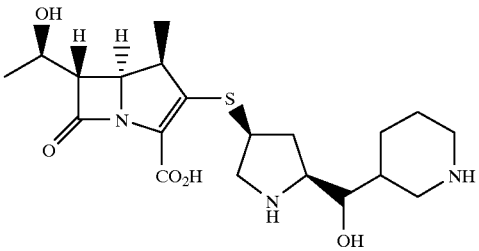

the compound represented by the following formula, and salts and esters thereof:

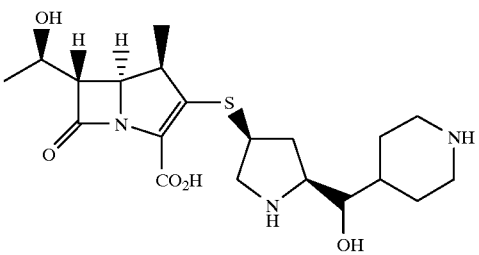

Next, a process for producing the compounds of the present invention will be described.

To produce a compound represented by the following general formula, or a salt thereof:

(I)

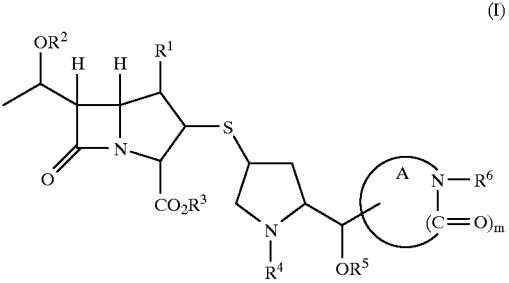

(wherein the ring A represents a 3- to 7-membered ring containing at least one nitrogen atom and optionally having a substituent other than $R^6$; $R^1$ represents hydrogen or methyl; $R^2$ and $R^5$ are the same or different and each represents hydrogen or a protecting group of the hydroxyl group; $R^3$ represents hydrogen or a protecting group of the carboxyl group; $R^4$ represents hydrogen, lower alkyl or a protecting group of the amino group; $R^6$ represents: (1)

hydrogen, (2) lower alkyl optionally substituted by optionally protected hydroxy, carbamoyl, formimidoyl, acetimidoyl or

(wherein $R^7$ and $R^8$ are the same or different and each represents hydrogen, lower alkyl, or a protecting group of the amino group), or (3) a protecting group of the amino group or a protecting group of the imino group; and m is 0 or 1), a compound represented by the following general formula (III), or a reactive derivative thereof:

(III)

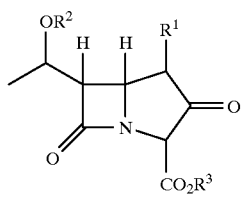

(wherein $R^1$ represents hydrogen or methyl; $R^2$ represents hydrogen or a protecting group of the hydroxyl group; and $R^3$ represents hydrogen or a protecting group of the carboxyl group) is reacted in the presence of a base with a mercaptan represented by the following general formula:

(IV)

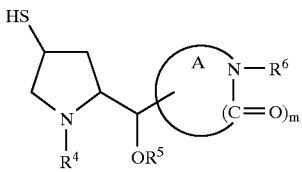

(wherein the ring A represents a 3- to 7-membered ring containing at least one nitrogen atom and optionally having a substituent other than $R^6$; $R^4$ represents hydrogen, lower alkyl or a protecting group of the amino group; $R^5$ represents hydrogen or a protecting group of the hydroxyl group; $R^6$ represents: (1) hydrogen, (2) lower alkyl optionally substituted by optionally protected hydroxy, carbamoyl, formimidoyl, acetimidoyl or

(wherein $R^7$ and $R^8$ are the same or different and each represents hydrogen, lower alkyl, or a protecting group of the amino group), or (3) a protecting group of the amino group or a protecting group of the imino group; and m is 0 or 1), optionally followed by the deblocking reaction. Thus, the compounds represented by the above general formula (I), or salts or esters thereof, can be produced. After eliminating the protecting group of $R^3$, $R^3$ represents a hydrogen atom.

To synthesize compounds represented by the above general formula (II) having particularly excellent antimicrobial effects, intermediates represented by the following general formulae are used as the substitutes respectively for the above-mentioned intermediates (III) and (IV):

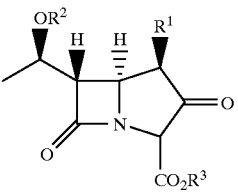

and

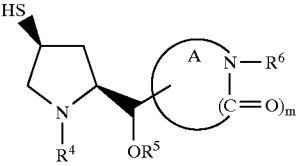

More particularly, reactive derivatives of the compounds represented by the general formula (III):

(III)

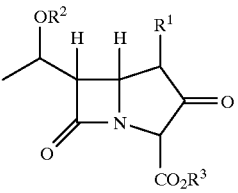

(wherein $R^1$ represents hydrogen or methyl; $R^2$ represents hydrogen or a protecting group of the hydroxyl group; and $R^3$ represents hydrogen or a protecting group of the carboxyl group) can be obtained by the following method. Thus, the above compound is reacted with an activating reagent in an inert organic solvent in the presence of a base to thereby give a reactive derivative represented by the following general formula:

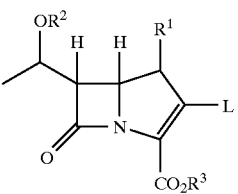

wherein $R^1$, $R^2$ and $R^3$ are each as defined above; and L represents a leaving group.

An arbitrary solvent may be used therefor, so long as it does not inhibit the reaction. Examples of such a solvent include diethyl ether, tetrahydrofuran, dioxane, dichloromethane, 1,2-dichloroethane, chloroform, carbon tetrachloride, trichloroethylene, hexane, benzene, chlorobenzene, toluene, ethyl acetate, butyl acetate, 1,2-dimethoxyethane, N,N-dimethylformamide, N,N-dimethylacetamide, dimethyl sulfoxide, hexamethylphosphoramide, acetone, acetonitrile, water and mixtures thereof.

As the base, use can be made of, for example, sodium carbonate, potassium carbonate, sodium hydride, potassium hydride, t-butoxypotassium, trimethylamine, triethylamine, N,N-diisopropylethylamine, N-methyl-morpholine, N-methyl-pyrrolidine, N-methylpiperidine, N,N-dimethylaniline, 1,8-diazabicyclo[5,4,0]undec-7-ene (DBU), pyridine, 4-dimethyl-aminopyridine, picoline, lutidine, quinoline and isoquinoline.

Examples of the activating reagent to be used in the reaction include acid anhydrides such as trifluoroacetic anhydride, methanesulfonic anhydride, trifluoromethane-sulfonic anhydride and p-toluene-sulfonic anhydride; and acid chlorides such as methanesulfonyl chloride, p-toluenesulfonyl chloride and diphenyl chlorophosphate.

In the above general formula, L represents a leaving group. Examples thereof include trifluoroacetoxy, methanesulfonyloxy, trifluoromethane-sulfonyloxy, p-toluenesulfonyloxy and diphenoxyphosphoryloxy groups.

The reaction is effected generally within a temperature range of −40 to 50° C., preferably −20 to 20° C.

The reaction between this reactive derivative and the mercaptan compound represented by the general formula

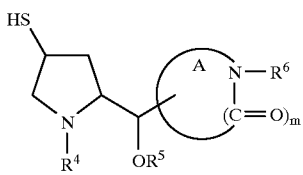

(wherein the ring A represents a 3- to 7-membered ring containing at least one nitrogen atom and optionally having a substituent other than $R^6$; $R^4$ represents hydrogen, lower alkyl or a protecting group of the amino group; $R^5$ represents hydrogen or a protecting group of the hydroxyl group; $R^6$ represents: (1) hydrogen, (2) lower alkyl optionally substituted by optionally protected hydroxy, carbamoyl, formimidoyl, acetimidoyl or

(wherein $R^7$ and $R^8$ are the same or different and each represents hydrogen, lower alkyl, or a protecting group of the amino group), or (3) a protecting group of the amino group or a protecting group of the imino group; and m is 0 or 1) is effected in the above-mentioned inert organic solvent with the use of a base. Subsequently, the obtained product is subjected to the deblocking reaction, if necessary. Thus the compound represented by the above general formula (I) or a salt or ester thereof can be obtained. Similar to the above-mentioned reaction, this reaction can be carried out generally within a temperature range of −40 to 50° C., preferably −20 to 20° C. It is possible to deblock the obtained compound as such without being purified. However, it is preferable to purify the product by any conventional method (for example, column chromatography with the use of silica gel, etc.) and then subject it to the deblocking reaction.

The protecting group may be eliminated by effecting, for example, reduction such as catalytic reduction or solvolysis under usual conditions, though the appropriate elimination method varies depending on the type of the protecting group.

The dose of the antimicrobial agent of the present invention varies depending on the severity of the conditions, age, sex and weight of the subject, the administration route, the disease, etc. Usually, it is administered to an adult in a dose of from 1 to 1,000 mg per day in one to several portions.

The administration route of the antimicrobial agent of the present invention is not particularly restricted. Namely, it can be orally or parenterally administered by any method commonly employed in the art.

The compounds of the present invention can be processed into pharmaceutical preparations by the conventional methods with the use of fillers, binders, lubricants, colorants, corrigents, etc. commonly employed in the art together with, if necessary, stabilizers, emulsifiers, sorbefacients, surfactants, etc.

To process the compounds of the present invention into pharmaceutical preparations, use may be made of, in particular, DHP-I inhibitors such as cilastatin.

The compounds of the present invention exhibit excellent antimicrobial activities on various Gram-positive and Gram-negative bacteria. To illustrate the usefulness of the compound of the present invention, the antimicrobial activities thereof on, in particular, P. aeruginosa, which has brought about clinical problems in recent years, will be given hereinbelow.

TABLE 1

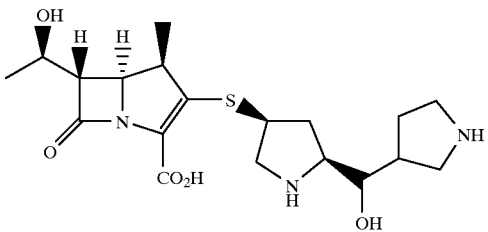

MIC (μg/ml)

| S. aureus E31295 | 0.1 |
|---|---|
| E. coli CS109 | 0.05 |
| H. influenzae IID1638 | 0.2 |
| P. aeruginosa E03763 | 0.8 |
| P. aeruginosa NCTC10490 | 0.1 |
| P. aeruginosa PA01 | 0.2 |
| P. aeruginosa E03441/SKR2-14 | 0.1 |
| P. aeruginosa E03441/SKR2/I-2 | 0.4 |
| P. aeruginosa E03441/WT | 0.2 |
| P. aeruginosa E03441/SKR2 | 0.2 |
| P. aeruginosa E03441/R24 | 3.13 |
| P. aeruginosa E03402 | 0.1 |

As the above Table 1 shows, the compound of the present invention has an excellent antimicrobial effect and, therefore, is useful in the prevention and treatment of various microorganisms.

To further illustrate the present invention in greater detail, and not by way of limitation, the following Examples will be given. In these Examples, $^1$H NMR spectra were measured by using a Varian FT NMR (400 MHz) spectrometer.

EXAMPLES

Production Example 1

(2S,4R)-N-tert-Butoxycarbonyl-4-tert-butyldimethylsiloxy-2-(N-tert-butyldimethylsilyl-2-oxoazetidin-3-ylhydroxymethyl)-pyrrolidine

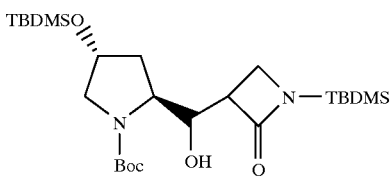

At −30° C., a 1.6 M solution of n-butyllithium in hexane (10.6 ml, 17.0 mmol) was added to a solution of diisopropylamine (2.6 ml, 19 mmol) in tetrahydrofuran (50 ml). After stirring at the same temperature for 20 minutes, the mixture was cooled to −78° C. Into the solution was dropped a solution of N-tert-butyldimethylsilyl-2-oxoazetidine (2.62 g, 14.2 mmol) in tetrahydrofuran (15 ml) and the resulting mixture was stirred at −78° C. for 20 minutes. Into the solution was dropped a solution of (2S,4R)-N-tert-butoxycarbonyl-4-tert-butyldimethylsiloxy-2-formyl-pyrrolidine (4.66 g, 14.2 mmol) in tetrahydrofuran (10 ml) and the resulting mixture was stirred at the same temperature for 40 minutes. To the reaction mixture was added a saturated aqueous solution of ammonium chloride (15 ml) and the mixture was returned to room temperature. Then water (50 ml) was added to the reaction mixture followed by extraction with diethyl ether (150 ml). The organic layer was washed successively with 1 N hydrochloric acid, water, a saturated aqueous solution of sodium hydrogencarbonate and a saturated aqueous solution of sodium chloride. Next, the organic layer was dried over anhydrous magnesium sulfate and concentrated under a reduced pressure. The residue was subjected to silica gel chromatography [Wakogel C-200, 100 g, hexane-ethyl acetate (9:1 to 4:1)] to thereby give the target compound (3.38 g, 35.5%).

NMR(CDCl$_3$) δ: 0.05, 0.06(6H, each s), 0.20, 0.23(6H, each s), 0.86(9H, s), 0.95, 0.96(9H, each s), 1.46(9H, s), 1.70~2.26(2H, m), 3.15~3.60(5H, m), 3.76~4.46(3H, m), 5.11(1H, d, J=9 Hz)

Production Example 2
(2S,4R)-N-tert-Butoxycarbonyl-4-tert-butyldimethylsiloxy-2-(2-oxoazetidin-3-ylhydroxymethyl)pyrrolidine

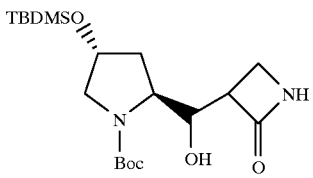

Under ice-cooling, acetic acid (0.52 ml, 9.1 mmol) and 1 M solution of tetrabutylammonium fluoride in tetrahydrofuran (9.1 ml, 9.1 mmol) were added to a solution of (2S,4R)-N-tert-butoxycarbonyl-4-tert-butyldimethylsiloxy-2-(N-tert-butyl-dimethylsilyl-2-oxoazetidin-3-ylhydroxymethyl)-pyrrolidine (3.34 g, 6.50 mmol) in tetrahydrofuran (35 ml) and the obtained mixture was stirred at the same temperature for 25 minutes. To this solution was added a saturated aqueous solution of sodium chloride (35 ml) followed by extraction with diethyl ether (150 ml). The organic layer was washed successively with water and a saturated aqueous solution of sodium chloride. Next, the organic layer was dried over anhydrous magnesium sulfate and concentrated under a reduced pressure. The residue was subjected to silica gel chromatography [Wakogel C-200, 25 g, hexane-ethyl acetate (3:1 to 1:2)] to thereby give the target compound (2.30 g, 88.5%).

NMR(CDCl$_3$) δ: 0.05, 0.06(6H, each s), 0.86, 0.87(9H, each s), 1.47(9H, s), 1.70~2.18(2H, m), 3.14~3.46(4H, m), 3.48~3.59(1H, m), 3.89~4.10(1H, m), 4.20~4.46(2H, m), 5.15(1H, d, J=8 Hz), 5.75(1H, br s)

Production Example 3
(2S,4R)-N-tert-Butoxycarbonyl-4-tert-butyldimethylsiloxy-2-[N-(p-nitrobenzyloxycarbonyl)azetidin-3-ylhydroxymethyl)-pyrrolidine

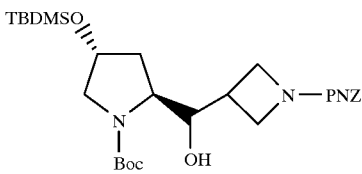

Under ice-cooling, a borane-methyl sulfide complex (2.3 ml, 23 mmol) was added to a solution of (2S, 4R)-N-tert-butoxycarbonyl-4-tert-butyldimethyl-siloxy-2-(2-oxoazetidin-3-ylhydroxymethyl)-pyrrolidine (1.84 g, 4.60 mmol) in tetra-hydrofuran (30 ml) and the obtained mixture was stirred at the same temperature for 30 minutes and then heated under reflux for 8.5 hours. The reaction mixture was cooled with ice and then methanol (15 ml) was added thereto. After stirring at the same temperature for 15 minutes, the solvent was distilled off under a reduced pressure. Then, methanol (20 ml) was added to the residue and the mixture was stirred at room temperature for 15 minutes followed by the distillation off of the solvent under a reduced pressure. To the solution obtained by dissolving the residue in tetrahydrofuran (20 ml) was added a solution of triethylamine (0.77 ml, 5.5 mmol) and p-nitro-benzyl chloroformate (1.09 g, 5.06 mmol) in tetrahydrofuran (5 ml) under ice-cooling. The obtained mixture was stirred at the same temperature for 3 hours. After adding ethyl acetate (150 ml) to the reaction mixture, the organic layer was washed successively with water and a saturated aqueous solution of sodium chloride. Next, the organic layer was dried over anhydrous magnesium sulfate and concentrated under a reduced pressure. The residue was subjected to silica gel chromatography [Wakogel C-200, 30 g, hexane-ethyl acetate (4:1 to 3:1)] to thereby give the target compound (450 mg, 17.3%).

NMR(CDCL$_3$) δ: 0.06(6H, s), 0.86(9H, s) 1.46, 1.47(9H, each s), 1.58~2.06(2H, m), 2.60~2.76(1H, m), 3.08~3.27 (1H, m), 3.45~3.59(1H, m), 3.63~3.73(1H, m), 3.74~4.50 (6H, m), 5.16(1H, d, J=19 Hz), 5.17(1H, d, J=19 Hz), 7.50, 7.55(2H, each d, J=8 Hz), 8.20, 8.23(2H, each d, J=8 Hz)

Production Example 4
(2S,4R)-4-Hydroxy-N-(p-nitrobenzyloxycarbonyl)-2-[N-(p-nitrobenzyloxycarbonyl)azetidin-3-ylhydroxymethyl)-pyrrolidine

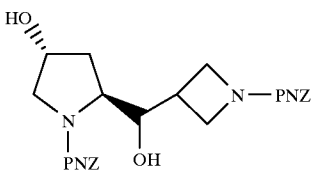

Under ice-cooling, trifluoroacetic acid (5 ml) was added to a solution of (2S,4R)-N-tert-butoxycarbonyl-4-tert-butyl-dimethylsiloxy-2-[N-(p-nitrobenzyloxycarbonyl)azetidin-3-ylhydroxymethyl]-pyrrolidine (527 mg, 0.933 mmol) in methylene chloride (5 ml) and the obtained mixture was stirred at the same temperature for 5 minutes and then at room temperature for additional 50 minutes. After distilling off the solvent and trifluoroacetic acid under a reduced pressure, the obtained residue was dissolved in tetrahydrofuran (7.5 ml). To this solution were added under ice-cooling triethylamine (0.53 ml, 3.8 mmol) and p-nitrobenzyl chloroformate (221 mg, 1.03 mmol) and the resulting mixture was stirred at the same temperature for 1 hour. After adding ethyl acetate (60 ml) to the reaction mixture, the organic layer was washed successively with water, 1 N hydrochloric acid, water, a saturated aqueous solution of sodium hydrogencarbonate and a saturated aqueous solution of sodium chloride. Next, the organic layer was dried over anhydrous magnesium sulfate and concentrated under a reduced pressure. To the solution of the residue thus obtained in tetrahydrofuran (6.5 ml) was added under ice-cooling a 1 M solution of tetrabutylammonium fluoride in tetrahydrofuran (1.9 ml, 1.9 mmol) and the obtained mixture was stirred at the same temperature for 30 minutes and then at room temperature for additional 3.0 hours. After distilling off the solvent under a reduced pressure, ethyl acetate (60 ml) was added to the residue. The organic layer was washed successively with water, a 50%-saturated aqueous solution of sodium chloride and a saturated aqueous solution of sodium chloride. The organic layer was dried over anhydrous magnesium sulfate and concentrated under a reduced pressure. The residue was subjected to silica gel chromatography (Wakogen C-200, 9 g, ethyl acetate) to thereby give the target compound (215 mg, 43.5%).

NMR(CDCl$_3$) δ: 1.75~2.25(2H, m), 2.50~2.76(1H, m), 3.44(1H, dd, J=3, 11 Hz), 3.71(1H, d, J=12 Hz), 3.83~4.31 (6H, m), 4.46(1H, br s), 5.14(2H, s), 5.21(1H, d, J=19 Hz), 5.22(1H, d, J=19 Hz), 7.43~7.53(4H, m), 8.16(4H, d, J=8 Hz)

Production Example 5
(2S,4S)-4-Acetylthio-N-(p-nitrobenzyloxycarbonyl)-2-[N-(p-nitrobenzyloxycarbonyl)azetidin-3-ylhydroxymethyl) pyrrolidine

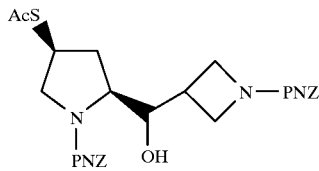

Under ice-cooling, triethylamine (0.10 ml, 0.72 mmol) and methanesulfonyl chloride (0.053 ml, 0.68 mmol) were added to a solution of (2S,4R)-4-hydroxy-N-(p-nitrobenzyloxycarbonyl)-2-[N-(p-nitrobenzyloxycarbonyl) azetidin-3-ylhydroxymethyl)-pyrrolidine (208 mg, 0.392 mmol) in methylene chloride (5 ml) and the obtained mixture was stirred at the same temperature for 1 hour. Then the reaction mixture was washed successively with water, a saturated aqueous solution of sodium hydrogen-carbonate and a saturated aqueous solution of sodium chloride. The organic layer was dried over anhydrous magnesium sulfate and concentrated under a reduced pressure. To the solution of the obtained residue in dimethylformamide (3 ml) was added potassium thioacetate (150 mg, 1.18 mmol) and the mixture was stirred at 70° C. for 3 hours. After distilling off the solvent under a reduced pressure, ethyl acetate (40 ml) was added to the residue. The organic layer was washed successively with water, a saturated aqueous solution of sodium hydrogen-carbonate, water and a saturated aqueous solution of sodium chloride. Next, the organic layer was dried over anhydrous magnesium sulfate and concentrated under a reduced pressure. The residue was subjected to silica gel chromatography [Wakogel C-200, 3 g, ethyl acetate-hexane (1:1)] to thereby give the target compound (129 mg, 56.0%).

NMR(CDCl$_3$) δ: 1.82~1.96(1H, m), 2.30(1H, td, J=7, 13 Hz), 2.34(3H, s), 2.63~2.76(1H, m), 3.09(1H, t, J=11 Hz), 3.50~4.09(6H, m), 4.13~4.27(2H, m), 5.17(2H, s), 5.22(2H, s), 7.50(2H, d, J=8 Hz), 7.51(2H, d, J=8 Hz), 8.18~8.27(4H, m)

Example 1
p-Nitrobenzyl (1R,5S,6S)-6-[(R)-1-hydroxyethyl]-1-methyl-2-{(2S,4S)-N-(p-nitrobenzyloxycarbonyl)-2-[N-(p-nitro-benzyl-oxycarbonyl)azetidin-3-ylhydroxy-methyl)-pyrrolidin-4-ylthio}-carbapen-2-em-3-carboxylate

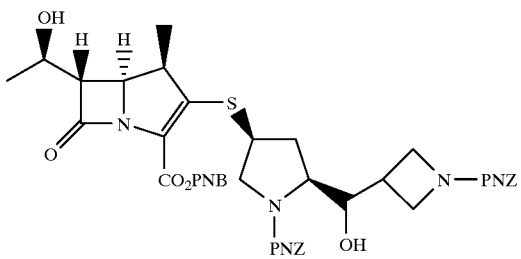

Under ice-cooling, a 1 N aqueous solution of sodium hydroxide (0.28 ml, 0.28 mmol) was added to a solution of (2S,4R)-4-acetylthio-N-(p-nitrobenzyloxy-carbonyl)-2-[N-(p-nitrobenzyloxycarbonyl)azetidin-3-ylhydroxymethyl)-pyrrolidine (129 mg, 0.219 mmol) in a mixture of methanol (1.5 ml) with tetrahydrofuran (1.5 ml) and the obtained mixture was stirred at the same temperature for 50 minutes. After adding 1 N hydrochloric acid (0.30 ml, 0.30 mmol) to the reaction mixture, the solvent was distilled off under a reduced pressure and ethyl acetate (25 ml) was added to the residue. Then, the organic layer was washed successively with water and a saturated aqueous solution of sodium chloride, dried over anhydrous magnesium sulfate and concentrated under a reduced pressure. To the solution of the obtained residue in acetonitrile (2 ml) were added, under ice-cooling, p-nitro-benzyl (1R,5S,6S)-2-diphenoxyphosphoryloxy-6-[(R)-1-hydroxy-ethyl]-1-methylcarbapen-2-em-3-carboxylate (118 mg, 1.99 mmol) and diisopropyl-ethylamine (0.036 ml, 0.21 mmol). The obtained mixture was stirred at the same temperature for 10 minutes and then at room temperature for additional 1 hour. After adding ethyl acetate (50 ml) to the reaction mixture, the organic layer was washed successively with water, a 50%-saturated aqueous solution of sodium chloride and a saturated aqueous solution of sodium chloride. Next, the organic layer was dried over anhydrous magnesium sulfate and concentrated under a reduced pressure. The residue was subjected to silica gel chromatography (Wakogel C-200, 3 g, 5% methanol-chloroform) to thereby give the target compound (137 mg, 70.3%).

NMR(CDCl$_3$) δ: 1.27(3H, d, J=7 Hz), 1.35(3H, d, J=7 Hz), 1.85~2.40(2H, m), 2.52~2.80(1H, m), 3.15~3.26(1H, m), 3.28(1H, dd, J=2, 7 Hz), 3.35(1H, dq, J=7, 7 Hz), 3.45~3.65(1H, m), 3.83~4.32(9H, m), 5.10~5.30(5H, m), 5.49(1H, d, J=13 Hz), 7.49(2H, d, J=8 Hz), 7.50(2H, d, J=8 Hz), 7.63(2H, d, J=8 Hz), 8.19(6H, d, J=8 Hz)

Example 2
(1R,5S,6S)-2-[(2S,4S)-2-(Azetidin-3-ylhydroxymethyl)-pyrrolidin-4-ylthio]-6-[(R)-1-hydroxyethyl]-1- methylcarbapen-2-em-3-carboxylic acid acetate

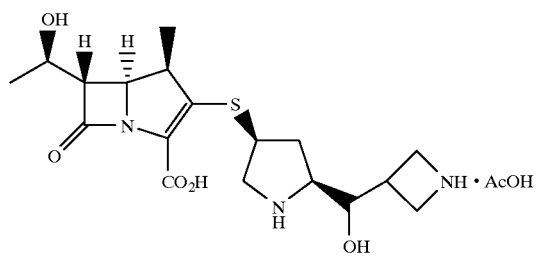

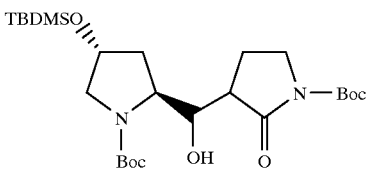

To a solution of p-nitrobenzyl (1R,5S,6S)-6-[(R)-1-hydroxyethyl]-1-methyl-2-{(2S,4S)-N-(p-nitro-benzyloxy-carbonyl)-2-[N-(p-nitrobenzyloxycarbonyl)-azetidin-3-ylhydroxymethyl)pyrrolidin-4-ylthio}-carbapen-2-em-3-carboxylate (137 mg, 0.154 mmol) in a mixture of a 0.1 M phosphate buffer (pH 7.0, 5 ml) with tetrahydrofuran (5 ml) was added 20% palladium hydroxide/carbon (0.14 g) and hydrogenation was effected by using a Perlman shaker under a moderate pressure (4 kg/cm²) at room temperature for 2 hours. After filtering off the catalyst through celite, the organic solvent was distilled off from the filtrate under a reduced pressure. The remaining aqueous layer was washed with diethyl ether and then the organic solvent was distilled off again from the aqueous layer under a reduced pressure. The pH value of the remaining aqueous layer was adjusted to 7.5 by using a 1 N aqueous solution of sodium hydroxide. After filtering off the insoluble matters, the filtrate was subjected to reversed phase silica gel chromatography (YMC SH-343-7 AM ODS, 0.005 M acetic acid-2.5% aqueous solution of methanol). The target fraction was concentrated and then freeze-dried. The diastereomer mixture thus obtained was subjected again to reversed phase silica gel chromatography (YMC SH-343-7 AM ODS, 0.02% ammonium acetate-5 to 20% aqueous solution of methanol) to thereby separate the diastereomers from each other. The target fractions were each concentrated and subjected again to reversed phase silica gel chromatography (YMC SH-343-7 AM ODS, 0.005 M acetic acid-3% aqueous solution of methanol) and each target fraction was concentrated and freeze-dried. Thus, the diastereomer A (7.9 mg, 11.2%, the compound of high polarity) and the diastereomer B (5.8 mg, 8.2%, the compound of low polarity) of the target compound were obtained.

Diastereomer A:

NMR(D₂O) δ: 1.15(3H, d, J=7 Hz), 1.23(3H, d, J=6 Hz), 1.74(1H, td, J=10, 14 Hz), 1.87(3H, s), 2.72(1H, ddd, J=7, 7, 14 Hz), 2.97~3.21(3H, m), 3.23~3.37(2H, m), 3.42(1H, dd, J=2, 6 Hz), 3.52(2H, d, J=10 Hz), 3.73~3.83(1H, m), 4.07(1H, dd, J=6, 12 Hz), 4.15~4.30(3H, m), 4.44(1H, d, J=4 Hz)

M.S. (m/e): 398(MH⁺)

Diastereomer B:

NMR(D₂O) δ: 1.16(3H, d, J=7 Hz), 1.23(3H, d, J=6 Hz), 1.88(3H, s), 2.16~2.25(1H, m), 2.52~2.65(1H, m), 2.72(1H, ddd, J=7, 7, 14 Hz), 3.18(1H, dd, J=7, 13 Hz), 3.24~3.39 (4H, m), 3.46(1H, dd, J=2, 6 Hz), 3.77(1H, dd, J=6, 13 Hz), 3.98~4.14(3H, m), 4.15~4.25(2H, m), 4.43(1H, dd, J=8, 9 Hz)

MS (m/e): 398(MH⁺)

Production Example 6

(2S,4R)-N-tert-Butoxycarbonyl-2-(N-tert-butoxycarbonyl-2-oxypyrrolidin-3-ylhydroxymethyl)-4-tert-butyldimethylsiloxy-pyrrolidine Under ice-cooling, a 1.7 M solution of n-butyl-lithium in hexane (113 ml, 192 mmol) was added to a solution of hexa-methyldisilazane (42.3 ml, 200 mmol) in tetrahydrofuran (300 ml). After stirring at the same temperature for 25 minutes, the reaction mixture was cooled to −78° C. Into this solution was dropped a solution of N-tert-butoxycarbonyl-2-oxo-pyrrolidine (337 g, 182 mmol) in tetrahydrofuran (150 ml) and the resulting mixture was stirred at −78° C. for 45 minutes. This solution was dropped into a solution of (2S,4R)-N-tert-butoxycarbonyl-4-tert-butyldimethylsiloxy-2-formylpyrrolidine (60.0 g, 182 mmol) in tetrahydrofuran (500 ml) cooled to −78° C. and stirred at the same temperature for 25 minutes. After adding a saturated aqueous solution of ammonium chloride (120 ml), the reaction mixture was returned to room temperature. Then the tetrahydrofuran was distilled off under a reduced pressure and ethyl acetate (900 ml) was added to the residue. The organic layer was washed successively with water, 1 N hydrochloric acid, water, a saturated aqueous solution of sodium hydrogencarbonate and a saturated aqueous solution of sodium chloride. The organic layer was dried over anhydrous magnesium sulfate and concentrated under a reduced pressure. The residue was subjected to silica gel chromatography [Merck, kieselgel 60, 1.4 kg, hexane-ethyl acetate (9:1 to 7:3)] to thereby give the diastereomer A (8.22 g, 8.8%, the compound of low polarity), the diastereomer B (28.3 g, 30.2%, the compound of moderate polarity) and the diastereomer C (24.1 g, 25.7%, the compound of high polarity) of the target compound.

Diastereomer A:

NMR(CDCl₃) δ: 0.06(6H, s), 0.88(9H, s), 1.45, 1.53(18H, each s), 1.80~2.13(3H, m), 2.40~2.50(1H, m), 2.55(1H, dd, J=9, 16 Hz), 3.31(1H, dd, J=4, 11 Hz), 3.48~3.68(3H, m), 3.77~3.85(1H, m), 4.32~4.43(2H, m), 5.62(1H, br s)

Diastereomer B:

NMR(CDCl₃) δ: 0.06(6H, s), 0.86(9H, s), 1.45, 1.53(18H, each s), 1.64~1.70(1H, m), 1.83~2.13(2H, m), 2.24(1H, td, J=5, 13 Hz), 2.40(1H, dd, J=11, 20 Hz), 3.28~3.62(3H, m), 3.77~3.98(2H, m), 4.13~4.54(3H, m)

Diastereomer C:

NMR(CDCl₃) δ: 0.06(6H, s), 0.86(9H, s), 1.45, 1.53(18H, each s), 1.82~1.92 (1H, m), 1. 94~2.05 (2H, m), 2.15~2.27 (1H, m), 2.54(1H, t, J=10 Hz), 3.23(1H, dd, J=4, 11 Hz), 3.51(1H, d, J=12 Hz), 3.56(1H, td, J=8, 11 Hz), 3.74~3.82 (1H, m), 4.18~4.48(3H, m)

Production Example 7

(2S,4R) -N-tert-Butoxycarbonyl-2- (N-tert-butoxycarbonyl-pyrrolidin-3-ylhydroxymethyl)-4-tert-butyldimethylsiloxy-pyrrolidine diastereomer A

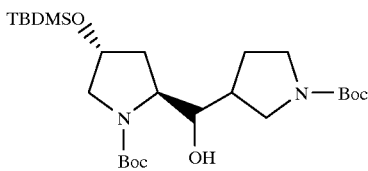

At room temperature, a borane-methyl sulfide complex (0.64 ml, 6.4 mmol) was added to a solution of (2S,4R)-N-tert-butoxycarbonyl-2-(N-tert-butoxy-carbonyl-2-oxopyrrolidin-3-ylhydroxymethyl)-4-tert-butyldimethylsiloxypyrrolidine diastereomer A (1.10 g, 2.14 mmol) in tetrahydrofuran (15 ml) and the obtained mixture was heated under reflux for 1.5 hours. After ice-cooling the reaction mixture, methanol (3 ml) was added thereto and the obtained mixture was stirred at the same temperature for 10 minutes. Then, the solvent was distilled off under a reduced pressure and the residue was subjected to silica gel chromatography [Wakogel C-200, 15 g, hexane-ethyl acetate (5:1)] to thereby give the target compound (825 mg, 77.1%).

NMR(CDCl$_3$) δ: 0.06(6H, s), 0.86(9H, s), 1.46(18H, s), 1.53~1.73(1H, m), 1.76~1.89(1H, m), 1.91~2.23(3H, m), 3.14~3.27(2H, m), 3.30~3.75(5H, m), 3.96(1H, q, J=8 Hz), 4.08~4.32(1H, m), 5.36, 5.44(1H, each brs)

Production Example 8
(2S, 4R)-4-Hydroxy-N-(p-nitrobenzyloxycarbonyl)-2-[N-(p-nitrobenzyloxycarbonyl)pyrrolidin-3-ylhydroxymethyl]-pyrrolidine diastereomer A

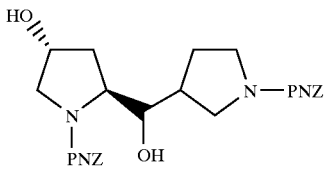

Under ice-cooling, trifluoroacetic acid (5 ml) was added to a solution of (2S,4R)-N-tert-butoxycarbonyl-2-(N-tert-butoxycarbonylpyrrolidin-3-ylhydroxymethyl)-4-tert-butyldi-methylsiloxy-pyrrolidine diasteromer A (815 mg, 1.63 mmol) in methylene chloride (5 ml) and the obtained mixture was stirred at the same temperature for 10 minutes and then at room temperature for an additional 1.5 hours. After distilling off the solvent and trifluoroacetic acid under a reduced pressure, the obtained residue was dissolved in tetrahydrofuran (13 ml). To this solution was added, under ice-cooling, a solution of triethylamine (1.4 ml, 10 mmol) and p-nitrobenzyl chloro-formate (0.74 g, 3.4 mmol) in tetrahydrofuran (4 ml) and the resulting mixture was stirred at the same temperature for 1 hour. After distilling off the solvent under a reduced pressure, ethyl acetate (40 ml) was added to the residue. Then, the organic layer was washed successively with water, 1 N hydrochloric acid, water, a saturated aqueous solution of sodium hydrogencarbonate and a saturated aqueous solution of sodium chloride. Next, the organic layer was dried over anhydrous magnesium sulfate and concentrated under a reduced pressure. To the solution of the residue thus obtained in tetrahydrofuran (15 ml) was added, under ice-cooling, a 1 M solution of tetrabutylammonium fluoride in tetrahydrofuran (2.25 ml, 2.25 mmol) and the obtained mixture was stirred at the same temperature for 10 minutes and then at room temperature for an additional 2.5 hours. After distilling off the solvent under a reduced pressure, ethyl acetate (40 ml) was added to the residue. The organic layer was washed successively with water, a 50%-saturated aqueous solution of sodium chloride and a saturated aqueous solution of sodium chloride. The organic layer was dried over anhydrous magnesium sulfate and concentrated under a reduced pressure. The residue was subjected to silica gel chromatography (Wakogel C-200, 8 g, ethyl acetate) to thereby give the target compound (393 mg, 44.3%).

NMR(CDCl$_3$) δ: 1.71~2.18(5H, m), 2.19~2.35(1H, m), 3.24~3.72(6H, m), 3.78~3.91(1H, m), 4.05~4.31(1H, m), 4.42~4.50(1H, m), 4.81~4.98(1H, m), 5.22(2H, s), 5.25, 5.26(2H, each s), 7.48~7.55(4H, m), 8.19~8.25(4H, m)

Production Example 9
(2S,4S)-4-Acetylthio-N-(p-nitrobenzyloxycarbonyl)-2-[N-(p-nitrobenzyloxycarbonyl)pyrrolidin-3-yl-hydroxymethyl]-pyrrolidine diastereomer A

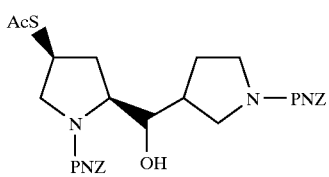

Under ice-cooling, triethylamine (0.13 ml, 0.93 mmol) and methanesulfonyl chloride (0.07 ml, 0.90 mmol) were added to a solution of (2S,4R)-4-hydroxy-N-(p-nitrobenzyloxycarbonyl)-2-[N-nitrobenzyloxy-carbonyl)-pyrrolidin-3-ylhydroxymethyl]-pyrrolidine diastereomer A (384 mg, 0.71 mmol) in methylene chloride (5 ml) and the obtained mixture was stirred at the same temperature for 30 minutes. Then, the reaction mixture was washed successively with water, a saturated aqueous solution of sodium hydrogencarbonate and a saturated aqueous solution of sodium chloride. The organic layer was dried over anhydrous magnesium sulfate and concentrated under a reduced pressure. To the solution of the obtained residue in dimethylformamide (5 ml) was added potassium thioacetate (242 mg, 2.12 mmol) and the mixture was stirred at 70° C. for 3.5 hours. After distilling off the solvent under a reduced pressure, ethyl acetate (40 ml) was added to the residue. The organic layer was washed successively with water, a saturated aqueous solution of sodium hydrogencarbonate, water and a saturated aqueous solution of sodium chloride. Next, the organic layer was dried over anhydrous magnesium sulfate and concentrated under a reduced pressure. The residue was subjected to silica gel chromatography [Wakogen C-200, 5 g, ethyl acetate-hexane (1:1)] to thereby give the target compound (203 mg, 47.8%).

NMR(CDCl$_3$) δ: 1.67~1.77(1H, m), 1.85~2.13(2H, m), 2.20~2.47(1H, m), 2.35, 2.36(3H, each s), 2.47~2.61 (1H, m), 3.17(1H, ddd, J=2, 10, 12 Hz), 3.26~3.54(3H, m), 3.56~3.75(2H, m), 3.80(1H, ddd, J=7, 9, 15 Hz), 3.91~4.03 (1H, m), 4.19~4.27(1H, m), 4.69~4.81(1H, m), 5.18~5.29 (4H, m), 7.52(4H, d, J=8 Hz), 8.19~8.27(4H, m)

Example 3
p-Nitrobenzyl (1R,5S,6S)-6-[(R)-1-hydroxyethyl]-1-methyl-2-{(2S,4S)-N-(p-nitrobenzyloxycarbonyl)-2-[N-(p-nitro-benzyloxy-carbonyl)-pyrrolidin-3-ylhydroxymethyl]-pyrrolidin-4-ylthio}-carbapen-2-em-3-carboxylate diastereomer A

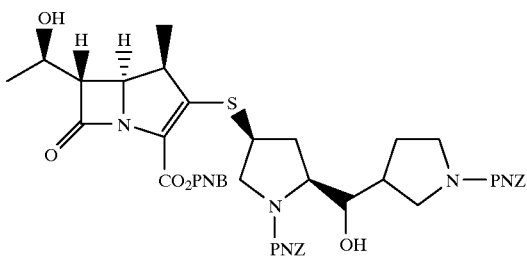

Under ice-cooling, a 1 N aqueous solution of sodium hydroxide (0.34 ml, 0.34 mmol) was added to a solution of (2S, 4S)-4-acetylthio-N-(p-nitrobenzyloxy-carbonyl)-2-[N-(p-nitrobenzyloxycarbonyl)pyrrolidin-3-ylhydroxymethyl]-pyrrolidine diastereomer A (196 mg, 0.33 mmol) in a mixture of methanol (3 ml) with tetrahydrofuran (3 ml) and the obtained mixture was stirred at the same temperature for 20 minutes. After adding 1 N hydrochloric acid (0.36 ml, 0.36 mmol) to the reaction mixture, the solvent was distilled off under a reduced pressure and ethyl acetate (30 ml) was added to the residue. Then, the organic layer was washed successively with water and a saturated aqueous solution of sodium chloride, dried over anhydrous magnesium sulfate and concentrated under a reduced pressure. To the solution of the obtained residue in acetonitrile (4 ml) were added, under ice-cooling, p-nitro-benzyl (1R,5S,6S)-2-diphenoxyphosphoryloxy-6-[(R)-1-hydroxyethyl]-1-methylcarbapen-2-em-3-carboxylate (177 mg, 0.30 mmol) and diisopropyl-ethylamine (0.055 ml, 0.32 mmol). The obtained mixture was stirred at the same temperature for 40 minutes and then at room temperature for an additional 1.5 hours. After adding ethyl acetate (40 ml) to the reaction mixture, the organic layer was washed successively with water, a 50%-saturated aqueous solution of sodium chloride and a saturated aqueous solution of sodium chloride. Next, the organic layer was dried over anhydrous magnesium sulfate and concentrated under a reduced pressure. The residue was subjected to silica gel chromatography (Wakogel C-200, 5 g, 1% methanol-chloroform) to thereby give the target compound (204 mg, 73.0%).

NMR(CDCl$_3$) δ: 1.28(3H, d, J=7 Hz), 1.38(3H, d, J=6 Hz), 1.69~1.82(1H, m), 1.79(1H, d, J=4 Hz), 1.88~2.15(2H, m), 2.20~2.40(1H, m), 2.41~2.64(1H, m), 3.21~3.80(9H, m), 3.92~4.07(1H, m), 4.07~4.21(1H, m), 4.23~4.30(2H, m), 5.15~5.30(5H, m), 5.50(1H, d, J=13 Hz), 7.52(4H, d, J=8 Hz), 7.65(2H, d, J=9 Hz), 8.18~8.27(6H, m)

Example 4

(1R,5S,6S)-6-[(R)-1-Hydroxyethyl]-1-methyl-2-[(2S,4S)-2-(pyrrolidin-3-ylhydroxymethyl)pyrrolidin-4-ylthio]-carbapen-2-em-3-carboxylic acid acetate diastereomer A

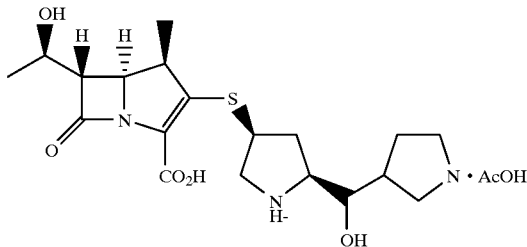

To a solution of p-nitrobenzyl (1R,5S,6S)-6-[(R)-1-hydroxyethyl]-1-methyl-2-{(2S,4S)-N-(p-nitrobenzyloxy-carbonyl)-2-[N-(p-nitrobenzyloxy-carbonyl)pyrrolidin-3-ylhydroxymethyl]pyrrolidin-4-ylthio}carbapen-2-em-3-carboxylate diastereomer A (204 mg, 0.127 mmol) in a mixture of a 0.1 M phosphate buffer (pH 7.0, 5 ml) with tetrahydrofuran (5 ml) was added 20% palladium hydroxide/carbon (205 mg) and hydrogenation was effected by using a Perlman shaker under a moderate pressure (4 kg/cm$^2$) at room temperature for 2 hours. After filtering off the catalyst through celite, the organic solvent was distilled off from the filtrate under a reduced pressure. The remaining aqueous layer was washed with diethyl ether and then the organic solvent was distilled off again from the aqueous layer under a reduced pressure. The pH value of the remaining aqueous layer was adjusted to 7.5 by using a 1 N aqueous solution of sodium hydroxide. After filtering off the insoluble matters, the filtrate was subjected to reversed phase silica gel chromatography (YMC SH-343-7 AM ODS, 0.005 M acetic acid-3% aqueous solution of methanol). The target fraction was concentrated and then freeze-dried to thereby give the target compound (41.7 mg, 40.7%).

NMR(D$_2$O) δ: 1.16(3H, d, J=7 Hz), 1.23(3H, d, J=6 Hz), 1.68~1.89(2H, m), 1.86(3H, s), 2.10~2.23(1H, m), 2.46~2.58(1H, m), 2.65(1H, td, J=7, 16 Hz), 3.13~3.46(7H, m), 3.60(1H, dd, J=7, 12 Hz), 3.67(1H, q, J=8 Hz), 3.92(1H, dd, J=6, 7 Hz), 3.94~4.03(1H, m), 4.14~4.24(2H, m)

M.S. (m/e): 412(MH$^+$)

Production Example 10

(2S,4R)-N-tert-Butoxycarbonyl-2-(N-tert-butoxycarbonyl-pyrrolidin-3-ylhydroxymethyl)-4-tert-butyldimethylsiloxy-pyrrolidine diastereomer B

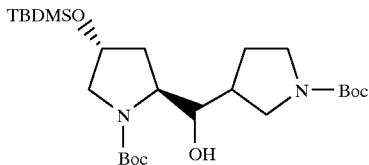

The reaction of Production Example 7 was repeated by using (2S,4R)-N-tert-butoxycarbonyl-2-(N-tert-butoxycarbonyl-2-oxopyrrolidin-3-ylhydroxymethyl)-4-tert-butyldimethyl-siloxypyrrolidine diastereomer B (4.51 g, 8.77 mmol) and the borane-methyl sulfide complex (2.6 ml, 26 mmol) to thereby give the target compound (3.52 g, 80.3%).

NMR(CDCl$_3$) δ: 0.06(6H, s), 0.86(9H, s), 1.45, 1.46(18H, each s), 1.65~2.20(5H, m), 3.08~3.73(6H, m), 3.90~4.20 (2H, m), 4.24~4.38(1H, m)

Production Example 11

(2S,4R)-4-Hydroxy-N-(p-nitrobenzyloxycarbonyl)-2-[N-(p-nitrobenzyloxycarbonyl)pyrrolidin-3-ylhydroxymethyl]-pyrrolidine diastereomer B

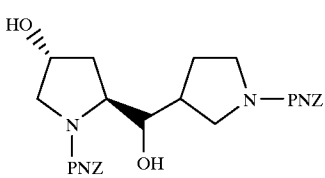

The reaction of Production Example 8 was repeated by using (2S,4R) -N-tert-butoxycarbonyl-2-(N-tert-butoxycarbonyl-pyrrolidin-3-ylhydroxymethyl)-4-tert-butyldimethylsiloxy-pyrrolidine diastereomer B (17.2 mg, 34.4 mmol) to thereby give the target compound (11.4 g, 61.0%).

NMR(CDCl₃) δ: 1.71~2.00(4H, m), 2.09~2.39(2H, m), 3.27 (1H, t, J=8 Hz), 3.36 (1H, td, J=7, 10 Hz), 3.48(1H, dd, J=3, 10 Hz), 3.56~3.88(3H, m), 4.12~4.25(2H, m), 4.48~4.54(1H, brs), 5.13~5.29(4H, m), 7.50(4H, d, J=8 Hz), 8.19(2H, d, J=8 Hz), 8.20(2H, d, J=8 Hz)

Production Example 12
(2S,4S)-4-Acetylthio-N-(p-nitrobenzyloxycarbonyl)-2-[N-(p-nitrobenzyloxycarbonyl)pyrrolidin-3-yl-hydroxymethyl]-pyrrolidine diastereomer B

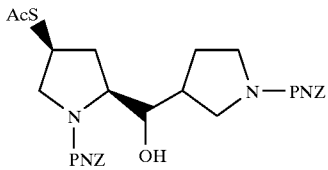

The reaction of Production Example 9 was repeated by using (2S,4R)-4-hydroxy-N-(p-nitrobenzyloxy-carbonyl)-2-[N-(p-nitrobenzyloxycarbonyl)pyrrolidin-3-ylhydroxymethyl]-pyrrolidine diastereomer B (10.3 g, 19.0 mmol) to thereby give the target compound (5.93 g, 51.9%).

NMR(CDCl₃) δ: 1.82~2.42(5H, m), 2.35(3H, s), 3.05~3.17(1H, m), 3.21~3.32(1H, m), 3.35(1H, dt, J=7, 10 Hz), 3.52~3.88(3H, m), 3.93~4.27(3H, m), 5.21(4H, s), 7.51(4H, d, J=8 Hz), 8.17~8.28(4H, m)

Example 5
p-Nitrobenzyl (1R,5S,6S)-6-[(R)-1-hydroxyethyl]-1-methyl-2-{(2S,4S)-N-(p-nitrobenzyloxycarbonyl)-2-[N-(p-nitro-benzyloxy-carbonyl)-pyrrolidin-3-ylhydroxymethyl]-pyrrolidin-4-ylthio}-carbapen-2-em-3-carboxylate diastereomer B

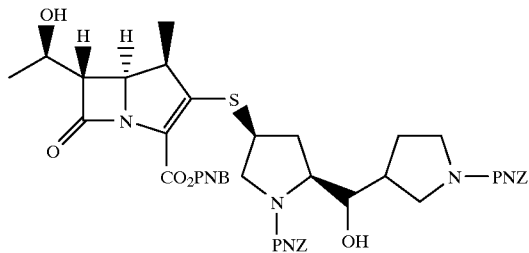

The reaction of Example 3 was repeated by using (2S,4S)-4-acetylthio-N-(p-nitrobenzyloxycarbonyl)-2-[N-(p-nitrobenzyl-oxycarbonyl)pyrrolidin-3-ylhydroxymethyl]-pyrrolidine diastereomer B (5.00 g, 8.30 mmol) to thereby give the target compound (6.40 g, 85.3%).

NMR(CDCl₃) δ: 1.28(3H, d, J=7 Hz), 1.37(3H, d, J=6 Hz), 1.50~2.53(5H, m), 3.15~3.45(5H, m), 3.47~3.82(3H, m), 3.90~4.32(5H, m), 5.14~5.29(5H, m), 5.50(1H, d, J=13 Hz), 7.45~7.55(4H, m), 7.65(2H, d, J=9 Hz), 8.17~8.26(6H, m)

Example 6
(1R,5S,6S)-6-[(R)-1-Hydroxyethyl]-1-methyl-2-[(2S,4S)-2-(pyrrolidin-3-ylhydroxymethyl)pyrrolidin-4-ylthio] carbapen-2-em-3-carboxylic acid acetate diastereomer B

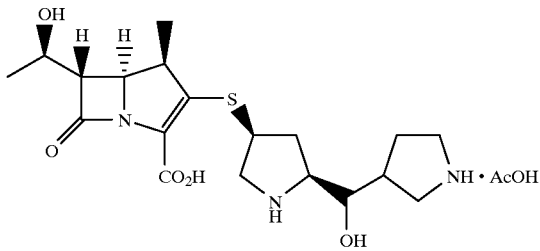

The reaction of Example 4 was repeated by using p-nitrobenzyl (1R,5S,6S)-6-[(R)-1-hydroxyethyl]-1-methyl-2-{(2S,4S)-N-(p-nitrobenzyloxycarbonyl)-2-[N-(p-nitrobenzyl-oxycarbonyl)pyrrolidin-3-ylhydroxymethyl] pyrrolidin-4-ylthio}carbapen-2-em-3-carboxylate diastereomer B (6.37 g, 7.05 mmol) to thereby give the target compound (1.25 g, 37.7%).

NMR(D₂O) δ: 1.16(3H, d, J=7 Hz), 1.23(3H, d, J=6 Hz), 1.65~1.78(1H, m), 1.78~1.90(1H, m), 1.85(3H, s), 2.07~2.18(1H, m), 2.43(1H, qd, J=9, 18 Hz), 2.57(1H, td, J=8, 14 Hz), 3.15(1H, dd, J=10, 12 Hz), 3.20~3.36(3H, m), 3.38~3.47(2H, m), 3.50(1H, dd, J=8, 12 Hz), 3.63(1H, dd, J=7, 12 Hz), 3.80(1H, ddd, J=4, 8, 12 Hz), 3.90~4.00(2H, m), 4.14~4.23(2H, m)

M.S. (m/e): 412(MH⁺)

Production Example 13
(2S,4R)-N-tert-Butoxycarbonyl-2-(N-tert-butoxycarbonyl-pyrrolidin-3-ylhydroxymethyl)-4-tert-butyldimethylsiloxy-pyrrolidine diastereomer C

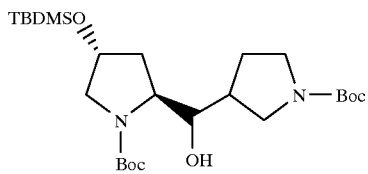

The reaction of Production Example 7 was repeated by using (2S,4R)-N-tert-butoxycarbonyl-2-(N-tert-butoxycarbonyl-2-oxopyrrolidin-3-ylhydroxymethyl)-4-tert-butyldimethyl-siloxypyrrolidine diastereomer C (24.1 g, 46.8 mmol) and the borane-methyl sulfide complex (25.3 ml, 253 mmol) to thereby give the target compound (20.2 g, 86.3%).

NMR(CDCl₃) δ: 0.06(6H, s), 0.86(9H, s), 1.46(18H, s), 1.56~2.24(5H, m), 2.85~3.32(3H, m), 3.34~3.71(3H, m), 3.80~4.20(2H, m), 4.24~4.42(1H, m)

Production Example 14
(2S,4R)-4-Hydroxy-N-(p-nitrobenzyloxycarbonyl)-2-[N-(p-nitrobenzyloxycarbonyl)pyrrolidin-3-ylhydroxymethyl]-pyrrolidine diastereomer C

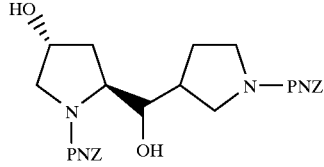

The reaction of Production Example 8 was repeated by using (2S,4S)-N-tert-butoxycarbonyl-2-(N-tert-butoxycarbonyl-pyrrolidin-3-ylhydroxymethyl)-4-tertbutyldimethylsiloxy-pyrrolidine diastereomer C (2.93 mg, 5.86 mmol) to thereby give the target compound (1.65 g, 51.8%).

NMR(CDCl$_3$) δ: 1.67~1.87(2H, m), 1.89~2.01(1H, m), 2.03~2.37(3H, m), 3.10~3.86(6H, m), 3.94~4.20(2H, m), 4.46~4.55(1H, m), 5.15~5.29(4H, m), 7.51(2H, d, J=8 Hz), 8.21(2H, d, J=8 Hz), 8.22(2H, d, J=8 Hz)

Production Example 15

(2S,4S)-4-Acetylthio-N-(p-nitrobenzyloxycarbonyl)-2-[N-(p-nitrobenzyloxycarbonyl)pyrrolidin-3-yl-hydroxymethyl]-pyrrolidine diastereomer C

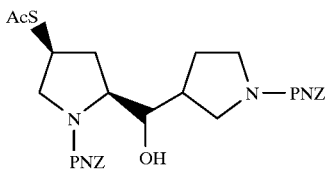

The reaction of Production Example 9 was repeated by using (2S,4R)-4-hydroxy-N-(p-nitrobenzyloxy-carbonyl)-2-[N-(p-nitrobenzyloxycarbonyl)pyrrolidin-3-ylhydroxymethyl]-pyrrolidine diastereomer C (7.93 g, 14.6 mmol) to thereby give the target compound (4.57 g, 52.0%).

NMR(CDCl$_3$) δ: 1.67~1.88(1H, m), 1.94~2.24(3H, m), 2.29~2.48(1H, m), 2.33, 2.34(3H, each s), 3.05~3.25(2H, m), 3.27~3.39(1H, m), 3.48~3.67(2H, m), 3.74~3.86(1H, m), 3.88~3.98(1H, m), 4.05~4.27(2H, m), 5.21(4H, s), 7.51 (4H, d, J=8 Hz), 8.19~8.27(4H, m)

Example 7 p-Nitrobenzyl (1R,5S,6S)-6-[(R)-1-hydroxyethyl]-1-methyl-2-{(2S,4S)-N-(p-nitrobenzyloxycarbonyl)-2-[N-(p-nitrobenzyloxy-carbonyl)-pyrrolidin-3-ylhydroxymethyl]pyrrolidin-4-ylthio}-carbapen-2-em-3-carboxylate diastereomer C

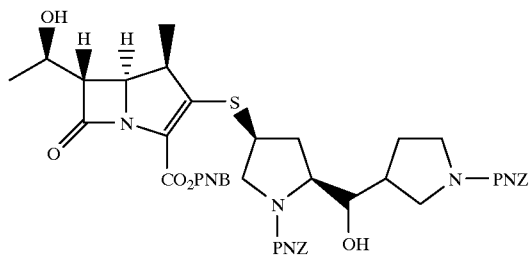

The reaction of Example 3 was repeated by using (2S,4S)-4-acetylthio-N-(p-nitrobenzyloxycarbonyl)-2-[N-(p-nitrobenzyl-oxycarbonyl)pyrrolidin-3-ylhydroxymethyl]-pyrrolidine diastereomer C (4.00 g, 6.64 mmol) to thereby give the target compound (5.04 g, 84.0%).

NMR(CDCl$_3$) δ: 1.28(3H, d, J=7 Hz), 1.38(3H, d, J=6 Hz), 1.50~2.50(5H, m), 3.08~3.43(5H, m), 3.46~3.69(3H, m), 3.84~4.31(5H, m), 5.15~5.29(5H, m), 5.50(1H, d, J=13 Hz), 7.44~7.57(4H, m), 7.65(2H, d, J=9 Hz), 8.17~8.27(6H, m)

Example 8

(1R,5S,6S)-6-[(R)-1-Hydroxyethyl]-1-methyl-2-[(2S,4S)-2-(pyrrolidin-3-ylhydroxymethyl)pyrrolidin-4-ylthio]carbapen-2-em-3-carboxylic acid acetate diastereomer C

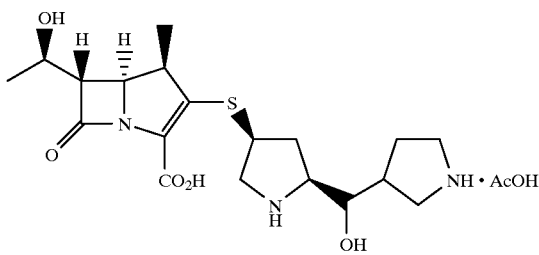

The reaction of Example 4 was repeated by using p-nitrobenzyl (1R,5S,6S)-6-[(R)-1-hydroxyethyl]-1-methyl-2-{(2S,4S)-N-(p-nitrobenzyloxycarbonyl)-2-[N-(p-nitrobenzyloxy-carbonyl)pyrrolidin-3-ylhydroxymethyl]pyrrolidin-4-ylthio}carbapen-2-em-3-carboxylate diastereomer C (4.99 g, 5.50 mmol) to thereby give the target compound (856 mg, 33.0%).

NMR(D$_2$O) δ: 1.16(3H, d, J=7 Hz), 1.23(3H, d, J=6 Hz), 1.81~1.94(2H, m), 1.87(3H, s), 2.13~2.23(1H, m), 2.45(1H, qd, J=8, 16 Hz), 2.60(1H, td, J=8, 14 Hz), 3.01(1H, dd, J=9, 11 Hz), 3.20~3.35(3H, m), 3.36~3.47(3H, m), 3.63(1H, dd, J=7, 12 Hz), 3.75(1H, ddd, J=4, 9, 10 Hz), 3.92~4.00(2H, m), 4.15~4.24(2H, m)

M.S. (m/e): 412 (MH$^+$)

Example 9

(1R,5S,6S)-6-[(R)-1-Hydroxyethyl]-1-methyl-2-[(2S,4S)-2-(pyrrolidin-3-ylhydroxymethyl)pyrrolidin-4-ylthio]carbapen-2-em-3-carboxylic acid hydrochloride diastereomer B

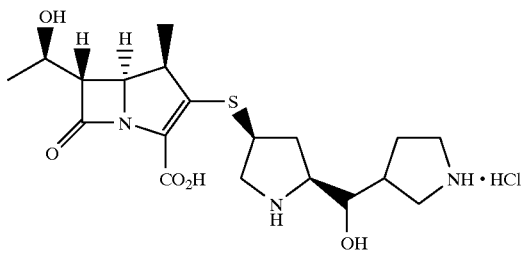

To a solution of p-nitrobenzyl (1R,5S,6S)-6-[(R)-1-hydroxyethyl]-1-methyl-2-{(2S,4S)-N-(p-nitro-benzyloxycarbonyl)-2-[N-(p-nitrobenzyloxycarbonyl)-pyrrolidin-3-ylhydroxymethyl}pyrrolidin-4-ylthio}carbapen-2-em-3-carboxylate diastereomer B (1.05 g, 1.16 mmol) in a mixture of a 0.1 M phosphate buffer (pH 7.0, 15 ml) with tetrahydrofuran (15 ml) was added 20% palladium hydroxide/carbon (1.05 g) and hydrogenation was effected by using a Perlman shaker under a moderate pressure (4 kg/cm$^2$) at room temperature for 2 hours. After filtering off the catalyst through celite, the organic solvent was distilled off from the filtrate under a reduced pressure. The remaining aqueous layer was washed with diethyl ether and then the organic solvent was distilled off again from the aqueous layer under a reduced pressure. After filtering off the insoluble matters, the pH value of the remaining aqueous layer was adjusted to 7.5 by using a 1 N aqueous solution of sodium hydroxide. Then, the filtrate was subjected to reversed phase silica gel chromatography (YMC SH-343-7 AM ODS, water –20% aqueous solution of methanol). The target fraction was concentrated and the pH value thereof was adjusted to 6.0 with 1 N hydrochloric acid. After freeze-drying, the target compound (147 mg, 28.3%) was obtained.

NMR(D₂O) δ: 1.17(3H, d, J=7 Hz), 1.24(3H, d, J=6 Hz), 1.73(1H, qd, J=9, 13 Hz), 1.84(1H, ddd, J=7, 10, 12 Hz), 2.07~2.18(1H, m), 2.44(1H, qd, J=9, 18 Hz), 2.58(1H, td, J=8, 14 Hz), 3.15(1H, dd, J=10, 12 Hz), 3.21 3.37(3H, m) 3.39~3.47(2H, m), 3.51(1H, dd, J=8, 12 Hz), 3.64(1H, dd, J=7, 12 Hz), 3.83(1H, ddd, J=3, 8, 11 Hz), 3.92~4.01(2H, m), 4.15~4.23(2H, m)

Production Example 16

(2S,4R)-N-tert-Butoxycarbonyl-2-(N-tert-butoxycarbonyl-2-oxopiperidin-3-ylhydroxymethyl)-4-tert-butyldimethyl-siloxy-pyrrolidine

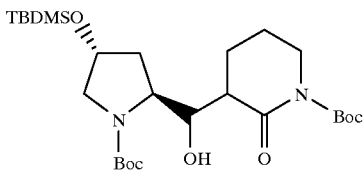

Under ice-cooling, a 2.5 M solution of n-butyl-lithium in hexane (12.6 ml, 31.5 mmol) was added to a solution of hexa-methyldisilazane (7.0 ml, 33 mmol) in tetrahydrofuran (50 ml). After stirring at the same temperature for 20 minutes, the reaction mixture was cooled to −78° C. Into this solution was dropped a solution of N-tert-butoxycarbonyl-2-oxopiperidine (5.97 g, 30.0 mmol) in tetrahydrofuran (30 ml) and the resulting mixture was stirred at −78° C. for 50 minutes. This solution was dropped into a solution of (2S,4R)-N-tert-butoxy-carbonyl-4-tert-butyldimethylsiloxy-2-formylpyrrolidine (9.87 g, 30.0 mmol) in tetrahydrofuran (100 ml) cooled to −78° C. and stirred at the same temperature for 40 minutes. After adding a saturated aqueous solution of ammonium chloride (20 ml), the reaction mixture was returned to room temperature. Then, the tetrahydrofuran was distilled off under a reduced pressure and ethyl acetate (220 ml) was added to the residue. The organic layer was washed successively with water, 1 N hydrochloric acid, water, a saturated aqueous solution of sodium hydrogen-carbonate and a saturated aqueous solution of sodium chloride. The organic layer was dried over anhydrous magnesium sulfate and concentrated under a reduced pressure. The residue was subjected to silica gel chromatography [Wakogel C-200, 150 g, hexane-ethyl acetate (9:1 to 3:1)] to thereby give the diastereomer A (5.50 g, 31.5%, the compound of low polarity) and the diastereomer B (3.62 g, 20.8%, the compound of high polarity) of the target compound were obtained.

Diastereomer A:

NMR(CDCl₃) δ: 0.06(6H, s), 0.86(9H, s), 1.44(9H, s), 1.51(9H, s), 1.67~2.00(4H, m), 2.17~2.44(2H, m), 3.29~3.80(5H, m), 3.88~4.33(3H, m), 4.45~4.53(2H, m)

Diastereomer B:

NMR(CDCl₃) δ: 0.06(6H, S), 0.86(9H, S), 1.45(9H, s), 1.52(9H, s) 1.77~1.96(3H, m), 2.09~2.26(2H, m), 2.50~2.63 (1H, m), 3.27(1H, dd, J=4, 11 Hz), 3.37~3.64(3H, m), 3.74~3.84(1H, m), 3.99~4.45(4H, m)

Production Example 17

(2S,4R)-N-tert-Butoxycarbonyl-2-(N-tert-butoxycarbonyl-piperidine-3-ylhydroxymethyl)-4-tert-butyldimethylsiloxy-pyrrolidine diastereomer A

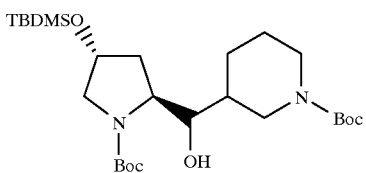

At room temperature, a borane-methyl sulfide complex (5.60 ml, 56.0 mmol) was added to a solution of (2S,4R)-N-tert-butoxycarbonyl-2-(N-tert-butoxycarbonyl-2-oxopiperidin-3-ylhydroxymethyl)-4-tert-butyldimethyl-siloxypyrrolidine diastereomer A (5.50 g, 10.4 mmol) in tetrahydrofuran (100 ml) and the obtained mixture was heated under reflux for 1.2 hours. After ice-cooling the reaction mixture, methanol (26 ml) was added thereto and the obtained mixture was stirred at the same temperature for 15 minutes. Then, the solvent was distilled off under a reduced pressure and the residue was subjected to silica gel chromatography [Wakogel C-200, 70 g, hexane-ethyl acetate (9:1 to 5:1)] to thereby give the target compound (2.99 g, 55.9%).

NMR(CDCl₃) δ: 0.06(6H, s), 0.86(9H, s), 1.45(18H, brs), 1.24~2.18(7H, m), 3.01~4.46(9H, m)

Production Example 18

(2S,4R)-4-Hydroxy-N-(p-nitrobenzyloxycarbonyl)-2-[N-(p-nitrobenzyloxycarbonyl)piperidine-3-ylhydroxymethyl]-pyrrolidine diastereomer A

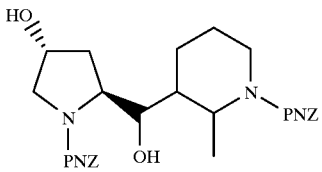

Under ice-cooling, trifluoroacetic acid (15 ml) was added to a solution of (2S,4R)-N-tert-butoxycarbonyl-2-(N-tert-butoxycarbonylpiperidin-3-ylhydroxymethyl)-4-tert-butyldi-methylsiloxy-pyrrolidine diastereomer A (2.94 g, 5.72 mmol) in methylene chloride (15 ml) and the obtained mixture was stirred at the same temperature for 10 minutes and then at room temperature for an additional 1.1 hours. After distilling off the solvent and trifluoroacetic acid under a reduced pressure, the obtained residue was dissolved in tetrahydro-furan (55 ml). To this solution was added, under ice-cooling, a solution of triethylamine (6.1 ml, 44 mmol) and p-nitrobenzyl chloroformate (2.59 g, 12.0 mmol) in tetrahydrofuran (15 ml) and the resulting mixture was stirred at the same temperature for 40 minutes. After distilling off the solvent under a reduced pressure, ethyl acetate (100 ml) was added to the residue. Then, the organic layer was washed successively with water, 1 N hydrochloric acid, water, a saturated aqueous solution of sodium hydrogencarbonate and a saturated aqueous solution of sodium chloride. Next, the organic layer was dried over anhydrous magnesium sulfate and concentrated under a reduced pressure. To the solution of the residue thus obtained in tetrahydrofuran (40 ml) was added, under ice-cooling, a 1 M solution of tetrabutylammonium fluoride in tetrahydrofuran (11.5 ml, 11.5 mmol) and the obtained mixture was stirred at the same temperature for 20 minutes and then at room temperature for an additional 4.0 hours. After distilling off the solvent under a reduced pressure, ethyl acetate (100 ml) was added to the residue. The organic layer was washed successively with water, a 50%-saturated aqueous solution of sodium chloride and a saturated aqueous solution of sodium chloride. The organic layer was dried over anhydrous magnesium sulfate and concentrated under a reduced pressure. The residue was subjected to silica gel chromatography (Wakogel C-200, 40 g, ethyl acetate) to thereby give the target compound (1.47 g, 46.1%).

NMR(CDCl$_3$) δ: 1.20~2.03(6H, m), 2.10~2.33(1H, m), 2.81~3.13(1H, m), 3.33~3.59(3H, m), 3.61~3.86(2H, m), 3.89~4.35(2H, m), 4.38~4.59(1H, m), 5.10~5.33(4H, m), 7.41~7.56(4H, m), 8.15~8.26(4H, m)

Production Example 19

(2S,4S)-4-Acetylthio-N-(p-nitrobenzyloxycarbonyl)-2-[N-(p-nitrobenzyloxycarbonyl)piperidine-3-yl-hydroxymethyl]-pyrrolidine diastereomer A Under ice-cooling, triethylamine (0.46 ml, 3.3 mmol) and methanesulfonyl chloride (0.25 ml, 3.2 mmol) were added to a solution of (2S,4R)-4-hydroxy-N-(p-nitro-benzyloxycarbonyl)-2-[N-(p-nitrobenzyloxycarbonyl)-piperidine-3-ylhydroxymethyl]-pyrrolidine diastereomer A (1.43 g, 2.56 mmol) in methylene chloride (15 ml) and the obtained mixture was stirred at the same temperature for 30 minutes. Then, the reaction mixture was washed successively with water, a saturated aqueous solution of sodium hydrogencarbonate and a saturated aqueous solution of sodium chloride. The organic layer was dried over anhydrous magnesium sulfate and concentrated under a reduced pressure. To the solution of the obtained residue in dimethylformamide (15 ml) was added potassium thioacetate (0.98 mg, 7.7 mmol) and the mixture was stirred at 70° C. for 5.5 hours. After distilling off the solvent under a reduced pressure, ethyl acetate (40 ml) was added to the residue. The organic layer was washed successively with water, a saturated aqueous solution of sodium hydrogencarbonate, water and a saturated aqueous solution of sodium chloride. Next, the organic layer was dried over anhydrous magnesium sulfate and concentrated under a reduced pressure. The residue was subjected to silica gel chromatography (wakogel C-200, 15 g, ethyl acetate-hexane (1:1)] to thereby give the target compound (890 mg, 56.4%).

NMR(CDCl$_3$) δ: 1.20~1.63(3H, m), 1.66~1.82(2H, m), 1.87~2.14(1H, m), 2.20~2.38(1H, m), 2.35(3H, s), 2.65~4.32(9H, m), 5.08~5.32(4H, m), 7.40~7.57(4H, m), 8.21(4H, d, J=9 Hz)

Example 10 p-Nitrobenzyl (1R,5S,6S)-6-[(R)-1-hydroxyethyl]-1-methyl-2-{(2S,4S)-N-(p-nitrobenzyloxycarbonyl)-2-[N-(p-nitro-benzyloxy-carbonyl)piperidine-3-ylhydroxymethyl]-pyrrolidin-4-ylthio}-carbapen-2-em-3-carboxylate diastereomer A Under ice-cooling, a 1 N aqueous solution of sodium hydroxide (1.48 ml, 1.48 mmol) was added to a solution of (2S,4S)-4-acetylthio-N-(p-nitrobenzyloxy-carbonyl)-2-[N-(p-nitrobenzyloxycarbonyl)piperidine-3-ylhydroxymethyl]-pyrrolidine diastereomer A (869 mg, 1.41 mmol) in a mixture of methanol (8.5 ml) with tetrahydrofuran (8.5 ml) and the obtained mixture was stirred at the same temperature for 30 minutes. After adding 1 N hydrochloric acid (1.55 ml, 1.55 mmol) to the reaction mixture, the solvent was distilled off under a reduced pressure and ethyl acetate (60 ml) was added to the residue. Then, the organic layer was washed successively with water and a saturated aqueous solution of sodium chloride, dried over anhydrous magnesium sulfate and concentrated under a reduced pressure. To the solution of the obtained residue in acetonitrile (10 ml) were added, under ice-cooling, p-nitrobenzyl (1R,5S,6S)-2-diphenoxyphosphoryloxy-6-[(R)-1-hydroxyethyl]-1-methylcarbapen-2-em-3-carboxylate (829 mg, 1. 40 mmol) and diisopropyl-ethylamine (0.26 ml, 1.5 mmol). The obtained mixture was stirred at the same temperature for 10 minutes and then at room temperature for an additional 4.5 hours. After adding ethyl acetate (70 ml) to the reaction mixture, the organic layer was washed successively with water, a 50%-saturated aqueous solution of sodium chloride and a saturated aqueous solution of sodium chloride. Next, the organic layer was dried over anhydrous magnesium sulfate and concentrated under a reduced pressure. The residue was subjected to silica gel chromatography (Wakogel C-200, 23 g, 2% methanol-chloroform) to thereby give the target compound (1.04 g, 80.3%).

NMR(CDCl$_3$) δ: 1.15~2.35(7H, m), 1.28(3H, d, J=7 Hz), 1.37(3H, d, J=6 Hz), 2.85~4.35(12H, m), 3.27(1H, dd, J=2.7 Hz), 5.10~5.35(5H, m), 5.50(1H, d, J=13 Hz), 7.40~7.60 (4H, m), 7.65(2H, d, J=9 Hz), 8.21(6H, d, J=9 Hz)

Example 11

(1R,5S,6S)-6-[(R)-1-Hydroxyethyl]-1-methyl-2-[(2S,4S)-2-piperidine-3-ylhydroxymethyl)pyrrolidin-4-ylthio]-carbapen-2-em-3-carboxylic acid acetate diastereomer A To a solution of p-nitrobenzyl (1R,5S,6S)-6-[(R)-1-hydroxyethyl]-1-methyl-2-{(2S,4S)-N-(p-nitro-benzyloxy-carbonyl)-2-[N- (p-nitrobenzyloxy-carbonyl)piperidine-3-ylhydroxymethyl]pyrrolidin-4-ylthio}carbapen-2-em-3- carboxylate diastereomer A (1.00 g, 1.09 mmol) in a mixture of a 0.1 M phosphate buffer (pH 7.0, 15 ml) with tetrahydrofuran (15 ml) was added 20% palladium hydroxide/carbon (1.0 g) and hydrogenation was effected by using a Perlman shaker under moderate pressure (4 kg/cm$^2$) at room temperature for 2 hours. After filtering off the catalyst through celite, the organic solvent was distilled off from the filtrate under a reduced pressure. The remaining aqueous layer was washed with diethyl ether and then the organic solvent was distilled off again from the aqueous layer under a reduced pressure. The pH value of the remaining aqueous layer was adjusted to 7.5 by using a 1 N aqueous solution of sodium hydroxide. After filtering off the insoluble matters, the filtrate was subjected to reversed phase silica gel chromatography (YMC SH-343-7 AM ODS, 0.005 M acetic acid-4% aqueous solution of methanol). The target fraction was concentrated and then freeze-dried to thereby give the target compound (193 mg, 36.4%).

NMR(D$_2$O) δ: 1.18(3H, d, J=7 Hz), 1.24(3H, d, J=6 Hz), 1.25~1.37(1H, m), 1.58~1.73(1H, m), 1.73~1.89(3H, m), 1.87(3H, s), 1.89~1.98(1H, m), 2.58(1H, td, J=8, 14 Hz), 2.77(1H, t, J=12 Hz), 2.87(1H, dd, J=3, 13 Hz), 3.27~3.40 (3H, m), 3.42(1H, dd, J=2, 6 Hz), 3.53~3.60(1H, m), 3.65 (1H, dd, J=7, 12 Hz), 3.80(1H, dd, J=3, 9 Hz), 3.90~4.01 (2H, m), 4.16~4.24(2H, m)

M.S. (m/e): 426(MH$^+$)

Production Example 20

(2S,4R)-N-tert-Butoxycarbonyl-2-(N-tert-butoxycarbonyl-piperidine-3-ylhydroxymethyl)-4-tert-butyldimethylsiloxy-pyrrolidine diastereomer B

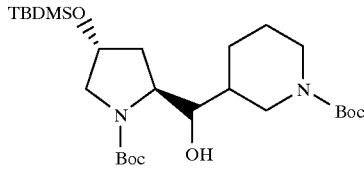

The reaction of Production Example 17 was repeated by using (2S,4R)-N-tert-butoxycarbonyl-2-(N-tert-butoxycarbonyl-2-oxopiperidin-3-ylhydroxymethyl)-4-tert-butyldimethylsiloxy-pyrrolidine diastereomer B (3.60 g, 6.82 mmol) and the borane methyl sulfide complex (2.05 ml, 20.5 mmol) to thereby give the target compound (2.50 9, 71.3%).

NMR(CDCl$_3$) δ: 0.06(6H, s), 0.86(9H, s), 1.46(18H, br s), 1.15~2.26(7H, m), 2.46~2.75(1H, m), 2.97~4.44(8H, m)

Production Example 21

(2S,4R)-4-Hydroxy-N-(p-nitrobenzyloxycarbonyl)-2-[N-(p-nitrobenzyloxycarbonyl)piperidine-3-ylhydroxymethyl]-pyrrolidine diastereomer B

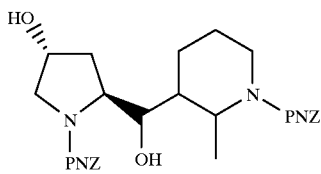

The reaction of Production Example 18 was repeated by using (2S,4R)-N-tert-butoxycarbonyl-2-(N-tert-butoxycarbonyl-piperidine-3-ylhydroxymethyl)-4-tert-butyldimethylsiloxy-pyrrolidine diastereomer B (2.48 mg, 4.82 mmol) to thereby give the target compound (778 mg, 28.9%).

NMR(CDCl$_3$) δ: 1.15~2.33(7H, m), 2.47~3.05(2H, m), 3.32~3.51(1H, m), 3.63~3.85(1H, m), 3.85~4.12(3H, m), 4.16~4.30(1H, m), 4.43~4.51(1H, m), 5.15~5.29(4H, m), 7.45~7.56(4H, m), 8.21(4H, d, J=9 Hz)

Production Example 22

(2S,4S)-4-Acetylthio-N-(p-nitrobenzyloxycarbonyl)-2-[N-(p-nitrobenzyloxycarbonyl)piperidine-3-yl-hydroxymethyl]-pyrrolidine diastereomer B

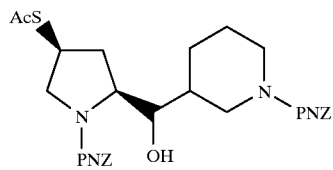

The reaction of Production Example 19 was repeated by using (2S,4R)-4-hydroxy-N-(p-nitrobenzyloxycarbonyl)-2-[N-(p-nitrobenzyloxy-carbonyl)piperidine-3-ylhydroxymethyl]pyrrolidine diastereomer B (757 mg, 1.36 mmol) to thereby give the target compound (555 mg, 66.2%).

NMR(CDCl$_3$) δ: 1.20~1.56(3H, m), 1.67~1.80(1H, m), 1.90~2.47(3H, m), 2.35(3H, s), 2.64~2.98(2H, m), 3.02~3.18(1H, m), 3.66~4.30(6H, m), 5.13~5.32(4H, m), 7.45~7.59(4H, m), 8.18~8.28(4H, m)

Example 12 p-Nitrobenzyl (1R,5S,6S)-6-[(R)-1-hydroxyethyl]-1-methyl-2-{(2S,4S)-N-(p-nitrobenzyloxycarbonyl)-2-[N-(p-nitrobenzyloxy-carbonyl)piperidine-3-ylhydroxymethyl]-pyrrolidin-4-ylthio}-carbapen-2-em-3-carboxylate diastereomer B

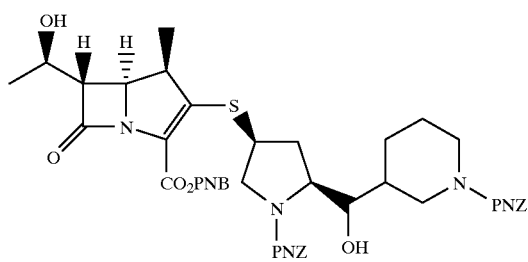

The reaction of Example 10 was repeated by using (2S,4S)-4-acetylthio-N-(p-nitrobenzyloxycarbonyl)-2-[N-(p-nitrobenzyloxycarbonyl)piperidine-3-ylhydroxymethyl]-pyrrolidine diastereomer B (540 mg, 0.877 mmol) to thereby give the target compound (589 mg, 73.2%).

NMR(CDCl$_3$) δ: 1.15~2.48(7H, m), 1.28(3H, d, J=7 Hz), 1.38(3H, d, J=6 Hz), 2.50~2.99(2H, m), 3.11~3.62(3H, m), 3.28(1H, dd, J=2, 7 Hz), 3.74~4.32(6H, m), 4.25(1H, dd, J=2, 9 Hz), 5.13~5.32(5H, m), 5.50(1H, d, J=13 Hz), 7.42~7.56(4H, m), 7.65(2H, d, J=9 Hz), 8.15~8.27(6H, m)

Example 13

(1R,5S,6S)-6-[(R)-1-Hydroxyethyl]-1-methyl-2-[(2S,4S)-2-piperidine-3-ylhydroxymethyl)pyrrolidin-4-ylthio]-carbapen-2-em-3-carboxylic acid acetate diastereomer B

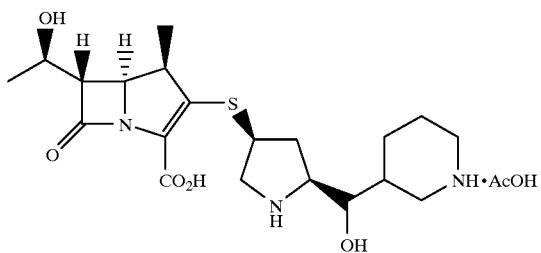

The reaction of Example 11 was repeated by using p-nitrobenzyl (1R,5S,6S)-6-[(R)-1-hydroxyethyl]-1-methyl-2-[(2S,4S)-N-(p-nitrobenzyloxycarbonyl)-2-[N-(p-nitrobenzyl-oxycarbonyl)-piperidine-3-ylhydroxymethyl)pyrrolidin-4-ylthio]-carbapen-2-em-3-carboxylate diastereomer B (560 mg, 0.610 mmol) to thereby give the target compound (119 mg. 40.0%).

NMR(D$_2$O) δ: 1.17(3H, d, J=7 Hz), 1.23(3H, d, J=6 Hz), 1.28~1.41(1H, m), 1.58~1.73(1H, m), 1.76~1.93(3H, m), 1.86(3H, s), 1.93~2.03(2H, m), 2.60(1H, td, J=8, 14 Hz), 2.83(1H, t, J=12 Hz), 2.86(1H, dt, J=3, 13 Hz), 3.26~3.40 (4H, m), 3.42(1H, dd, J=2, 6 Hz), 3.61(1H, dd, J=7, 12 Hz), 3.77~3.85(2H, m), 3.92~4.02(1H, m), 4.15~4.24(2H, m)

M.S. (m/e): 426(MH$^+$)

Production Example 23
(2S,4R)-2-(N-Benzylpiperidin-4-ylhydroxymethyl)-N-tert-butoxycarbonyl-4-tert-butyldimethylsiloxy-pyrrolidine At 55° C., a catalytic amount of iodine and ethyl bromide (0.075 ml) were added to a suspension (4 ml) of a magnesium powder (486 mg, 20.0 mmol) in tetrahydrofuran. Into the obtained solution was dropped, under heating, a solution of N-benzyl-4-chloropiperidine (4.61 g, 20.0 mmol) in tetrahydrofuran (25 ml) over 20 minutes. After the completion of the dropping, the resulting mixture was heated under reflux for 1 hour. The solution was cooled by allowing it to stand and then dropped into a solution of (2S,4R)-N-tert-butoxycarbonyl-4-tert-butyldimethyl-siloxy-2-formylpyrrolidine (6.58 g, 20.0 mmol) in tetrahydrofuran (60 ml) cooled to −30° C. After the completion of the dropping, the reaction mixture was stirred for 1 hour while slowly returning to room temperature. After adding a saturated aqueous solution of ammonium chloride (20 ml) to the reaction mixture, the tetrahydrofuran was distilled off under a reduced pressure. Then, ethyl acetate (120 ml) was added to the residue. The organic layer was washed successively with water, 1 N hydrochloric acid, water, a 10% aqueous solution of potassium carbonate, water and a saturated aqueous solution of sodium chloride. The organic layer was dried over anhydrous magnesium sulfate and concentrated under a reduced pressure. The residue was subjected to silica gel chromatography [Wakogel C-200, 100 g, hexane-ethyl acetate (3:1 to 1:1)] to thereby give the target compound (3.40 g, 33.7%).

NMR(CDCl$_3$) δ: 0.05(6H, s), 0.86(9H, s), 1.20~1.33(1H, m), 1.36~2.00(8H, m), 1.46(9H, s), 2.84~2.99(2H, m), 3.20~3.31(1H, m), 3.21(1H, dd, J=4, 12 Hz), 3.48(1H, d, J=16 Hz), 3.49(1H, d, J=16 Hz), 3.56(1H, d, J=12 Hz), 4.10(1H, q, J=8 Hz), 4.25(1H, brs), 5.02(1H, brs), 7.19~7.36 (5H, m)

Production Example 24
(2S,4R)-N-tert-Butoxycarbonyl-4-tert-butyldimethylsiloxy-2-[N-(p-nitrobenzyloxycarbonyl)-piperidine-4-ylhydroxymethyl]-pyrrolidine To a solution of (2S,4R)-2-(N-benzylpiperidin-4-ylhydroxymethyl]-N-tert-butoxycarbonyl-4-tert-butyldimethyl-siloxypyrrolidine (748 mg, 1.48 mmol) in methanol (10 ml) were added ammonium formate (0.47 g, 7.5 mmol) and 10% palladium-carbon (0.75 g) and the obtained mixture was heated under reflux for 15 minutes. After filtering off the catalyst through celite, the solvent was distilled off. Then a 5% aqueous solution of potassium carbonate (15 ml) was added to the residue followed by extraction with ethyl acetate. The organic layer was washed with a saturated aqueous solution of sodium chloride, dried over anhydrous magnesium sulfate and concentrated under a reduced pressure. To the solution of the residue thus obtained in tetrahydrofuran (10 ml) were added, under ice-cooling, triethylamine (0.18 ml, 1.3 mmol) and p-nitrobenzyl chloroformate (255 mg, 1.18 mmol) and the mixture was stirred at the same temperature for 6 hours. After adding ethyl acetate (60 ml) to the reaction mixture, the organic layer was washed successively with water, 1 N hydrochloric acid, water, a saturated aqueous solution of sodium hydrogen-carbonate and a saturated aqueous solution of sodium chloride. The organic layer was dried over anhydrous magnesium sulfate and concentrated under a reduced pressure to thereby give the target compound as a crude product (624 mg, 71.1%).

NMR(CDCl$_3$) δ: 0.05(6H, s), 0.86(9H, s), 1.40~1.85(6H, m), 1.46(9H, s), 1.90~2.02(1H, m), 2.60~2.92(2H, m), 3.22 (1H, dd, J=4, 12 Hz), 3.31(1H, d, J=8 Hz), 3.61(1H, d, J=12 Hz), 4.12(1H, q, J=8 Hz), 4.16~4.37(3H, m), 5.15~5.40(3H, m), 7.50(2H, d, J=8 Hz), 8.21(2H, d, J=8 Hz)

Production Example 25
(2S,4R)-4-Hydroxy-N-(p-nitrobenzyloxycarbonyl)-2-[N-(p-nitrobenzyloxycarbonyl)piperidine-4-ylhydroxymethyl]-pyrrolidine Under ice-cooling, trifluoroacetic acid (20 ml) was added to a solution of crude (2S,4R)-N-tert-butoxycarbonyl-4-tert-butyldimethylsiloxy-2-[N-(p-nitrobenzyloxycarbonyl) piperidine-4-ylhydroxymethyl]-pyrrolidine (3.89 g. 6.56 mmol) in methylene chloride (20 ml) and the obtained mixture was stirred at the same temperature for 40 minutes and then at room temperature for additional 40 minutes.

Next, the solvent and trifluoro-acetic acid were distilled off under a reduced pressure. A 10% aqueous solution of potassium carbonate (30 ml) was added to the residue followed by extraction with ethyl acetate. The organic layer was washed with a saturated aqueous solution of sodium chloride, dried over anhydrous magnesium sulfate and concentrated. The residue thus obtained was dissolved in tetrahydrofuran (30 ml). To the solution thus obtained was added, under ice-cooling, a solution of triethylamine (0.94 ml, 6.7 mmol) and p-nitrobenzyl chloroformate (1.39 g, 6.45 mmol) in tetrahydrofuran (15 ml) and the resulting mixture was stirred at the same temperature for 10 minutes and then at room temperature for an additional 2.5 hours. After adding ethyl acetate (120 ml) to the reaction mixture, the organic layer was washed successively with water, 1 N hydrochloric acid, water, a saturated aqueous solution of sodium hydrogen-carbonate and a saturated aqueous solution of sodium chloride. The organic layer was dried over anhydrous magnesium sulfate and concentrated under a reduced pressure. The residue was dissolved in tetrahydrofuran (40 ml). To the obtained solution was added, under ice-cooling, a 1 M solution of tetrabutyl-ammonium fluoride in tetrahydrofuran (8.9 ml, 8.9 mmol) and the mixture was stirred at the same temperature for 15 minutes and then at room temperature for an additional 2 hours. After distilling off the solvent under a reduced pressure, ethyl acetate (80 ml) was added to the residue. The organic layer was washed successively with water, 1 N hydrochloric acid, a 50%-saturated aqueous solution of sodium chloride, a saturated aqueous solution of sodium hydrogen-carbonate and a saturated aqueous solution of sodium chloride, dried over anhydrous magnesium sulfate and concentrated under a reduced pressure. The residue was subjected to silica gel chromatography (Wakogel C-200, 35 g, ethyl acetate) to thereby give the target compound (2.00 g, 54.6%).

NMR(CDCl$_3$) δ: 1.45~1.76(5H, m), 1.77~1.95(1H, m), 2.06~2.16(1H, m), 2.60~2.90(2H, m), 3.30~3.50(2H, m), 3.82(1H, d, J=12 Hz), 4.15~4.35(3H, m), 4.46(1H, brs), 4.65~4.86(1H, m), 5.15~5.28(4H, m), 7.50(2H, d, J=8 Hz), 7.51(2H, d, J=8 Hz), 8.22(4H, d, J=8 Hz)

Production Example 26
(2S,4S)-4-Acetylthio-N-(p-nitrobenzyloxycarbonyl)-2-[N-(p-nitrobenzyloxycarbonyl)piperidine-4-yl-hydroxymethyl]-pyrrolidine Under ice-cooling, triethylamine (0.68 ml, 4.9 mmol) and methanesulfonyl chloride (0.36 ml, 4.7 mmol) were added to a solution of (2S,4R)-4-hydroxy-N-(p-nitrobenzyloxycarbonyl)-2-[N-(p-nitrobenzyloxycarbonyl) piperidine-4-ylhydroxymethyl]-pyrrolidine (1.99 g, 3.57 mmol) in methylene chloride (20 ml) and the obtained mixture was stirred at the same temperature for 2 hours. Then, the reaction mixture was washed successively with water, a saturated aqueous solution of sodium hydrogencarbonate and a saturated aqueous solution of sodium chloride. The organic layer was dried over anhydrous magnesium sulfate and concentrated under a reduced pressure. To the solution of the obtained residue in dimethylformamide (20 ml) was added potassium thioacetate (1.22 g, 10.7 mmol) and the mixture was stirred at 70° C. for 3 hours. After distilling off the solvent under a reduced pressure, ethyl acetate (50 ml) was added to the residue. The organic layer was washed successively with water, a saturated aqueous solution of sodium hydrogen-carbonate, water and a saturated aqueous solution of sodium chloride. Next, the organic layer was dried over anhydrous magnesium sulfate and concentrated under a reduced pressure. The residue was subjected to silica gel chromatography [Wakogel C-200, 20 g, ethyl acetate-hexane (1:1 to 2:1)] to thereby give the target compound (1.57 g, 71.4%).

NMR(CDCl$_3$) δ: 1.48~2.10(6H, m), 2.36(3H, s), 2.45~2.60(1H, m), 2.63~2.93(2H, m), 3.18(1H, dd, J=9, 11 Hz), 3.42~3.51(1H, m), 3.77~3.88(1H, m), 4.10(1H, q, J=8 Hz), 4.15~4.40(3H, m), 4.50~4.75(1H, m), 5.15~5.29(4H, m), 7.46~7.55(4H, m), 8.17~8.26(4H, m)

Example 14
p-Nitrobenzyl (1R,5S,6S)-6-[(R)-1-hydroxyethyl]-1-methyl-2-{(2S,4S)-N-(p-nitrobenzyloxycarbonyl)-2-[N-(p-nitro-benzyloxy-carbonyl)piperidine-4-ylhydroxymethyl]-pyrrolidin-4-ylthio}-carbapen-2-em-3-carboxylate Under ice-cooling, a 1 N aqueous solution of sodium hydroxide (2.66 ml, 2.66 mmol) was added to a solution of (2S,4S)-4-acetylthio-N-(p-nitrobenzyloxy-carbonyl)-2-[N-(p-nitrobenzyloxycarbonyl)piperidine-3-ylhydroxymethyl]-pyrrolidine (1.56 g, 2.53 mmol) in a mixture of methanol (15 ml) with tetrahydrofuran (15 ml) and the obtained mixture was stirred at the same temperature for 30 minutes. After adding 1 N hydrochloric acid (2.75 ml, 2.75 mmol) to the reaction mixture, the solvent was distilled off under a reduced pressure and ethyl acetate (60 ml) was added to the residue. Then, the organic layer was washed successively with water and a saturated aqueous solution of sodium chloride, dried over anhydrous magnesium sulfate and concentrated under a reduced pressure. To the solution of the obtained residue in acetonitrile (20 ml) were added, under ice-cooling, p-nitrobenzyl (1R,5S,6S)-2-diphenoxyphosphoryloxy-6-[(R)-1-hydroxyethyl]-1-methylcarbapen-2-em-3-carboxylate (1.46 g, 2.46 mmol) and diisopropyl-ethylamine (0.45 ml, 2.6 mmol). The obtained mixture was stirred at the same temperature for 40 minutes and then at room temperature for an additional 40 minutes. After adding ethyl acetate (100 ml) to the reaction mixture, the organic layer was washed successively with water, a 50%-saturated aqueous solution of sodium chloride and a saturated aqueous solution of sodium chloride. Next, the organic layer was dried over anhydrous magnesium sulfate and concentrated under a reduced pressure. The residue was subjected to silica gel chromatography (Wakogel C-200, 40 g, 1% methanol-chloroform) to thereby give the target compound (1.03 g, 44.6%).

NMR(CDCl$_3$) δ: 1.28(3H, d, J=8 Hz), 138(3H, d, J=7 Hz), 1.45~2.00(6H, m), 2.47~260(1H, m), 2.63~2.93(2H, m), 3.18~3.40(2H, m), 3.28(1H, dd, J=2, 7 Hz), 3.40~3.63(2H, m), 4.05~4.40(6H, m), 5.15~5.32(5H, m), 5.50(1H, d, J=13 Hz), 7.47~7.55(4H, m), 7.65(2H, d, J=8 Hz), 8.18~8.27(6H, m)

Example 15

(1R,5S,6S)-6-[(R)-1-Hydroxyethyl]-1-methyl-2-[(2S,4S)-2-piperidine-4-ylhydroxymethyl)pyrrolidin-4-ylthio]carbapen-2-em-3-carboxylic acid acetate

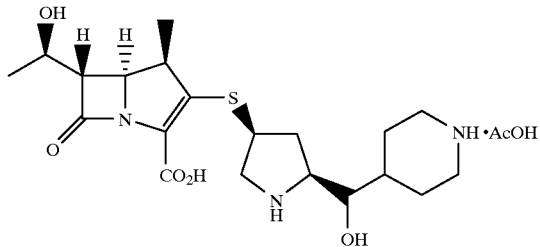

To a solution of p-nitrobenzyl (1R,5S,6S)-6-[(R)-1-hydroxyethyl]-1-methyl-2-{(2S,4S)-N-(p-nitrobenzyloxycarbonyl)-2-[N-(p-nitrobenzyloxycarbonyl)-piperidine-4-ylhydroxymethyl]pyrrolidin-4-ylthio}carbapen-2-em-3-carboxylate (1.03 g, 1.12 mmol) in a mixture of a 0.1 M phosphate buffer (pH 7.0, 20 ml) with tetrahydrofuran (20 ml) was added 20% palladium hydroxide/carbon (1.03 g) and hydrogenation was effected by using a Perlman shaker under a moderate pressure (4 kg/cm$^2$) at room temperature for 1.5 hours. After filtering off the catalyst through celite, the organic solvent was distilled off from the filtrate under a reduced pressure. The remaining aqueous layer was washed with diethyl ether and then the organic solvent was distilled off again from the aqueous layer under a reduced pressure. The pH value of the remaining aqueous layer was adjusted to 7.5 by using a 1 N aqueous solution of sodium hydroxide. After filtering off the insoluble matters, the filtrate was subjected to reversed phase silica gel chromatography (YMC SH-343-7 AM ODS, 0.005 M acetic acid-2% aqueous solution of methanol). The target fraction was concentrated and then freeze-dried to thereby give the target compound (178 mg, 32.7%).

NMR(D$_2$O) δ: 1.17(3H, d, J=7 Hz), 1.24(3H, d, J=6 Hz), 1.50~1.90(6H, m), 1.86(3H, s), 2.65(1H, td, J=8, 14 Hz), 2.97(2H, q, J=13 Hz), 3.27~3.38(2H, m), 3.38~3.50(3H, m), 3.61(1H, dd, J=6, 12 Hz), 3.72~3.83(2H, m), 3.95~4.05(1H, m), 4.14~4.24(2H, m)

M.S. (m/e): 426(MH$^+$)

We claim:

1. A carbapenem compound represented by the following formula (I), or a salt thereof:

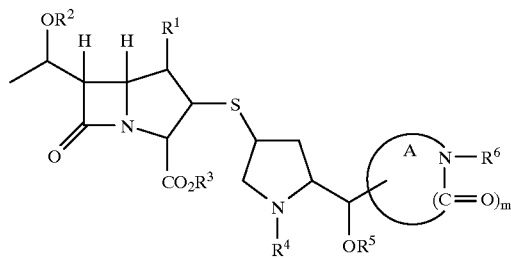

(I)

wherein the ring A represents a 3- to 7-membered saturated or partially unsaturated heterocycle containing only nitrogen as heteroatoms and optionally having a ring substituent other than R$^6$ and selected from the group consisting of a hydrogen atom, hydroxyl, mercapto, halogen, cyano, azido, alkyl, alkenyl, alkynyl, alkoxy, halogenoalkyl, guanidino, formimidoyl, acetimidoyl, carbamoyl, thiocarbamoyl, carbamoylalkyl, carbamido, alkanoyl, amino, alkylamino, dialkylamino, aminoalkyl, carboxy, alkoxycarbonyl, alkoxycarbonylalkyl, aminoalkylaminoalkyl, alkylcarbonyloxy, cycloalkyl, cycloalkenyl, phenyl, alkylthio, phenylthio, benzyl, benzoyl and halogenoaryl; R$^1$ represents hydrogen or methyl; R$^2$ and R$^5$ are the same or different and each represents hydrogen or a protecting group of the hydroxyl group selected from the group consisting of trimethylsilyl, t-butyl dimethylsilyl, methoxymethyl, 2-methoxyethoxymethyl, tetrahydropyranyl, benzyl, p-methoxybenzyl, 2,4-dimethoxybenzyl, o-nitrobenzyl, p-nitrobenzyl, trityl, formyl, acetyl, t-butoxy-carbonyl, 2-iodoethoxycarbonyl, 2,2,2-trichloroethoxy-carbonyl, 2-propenyloxycarbonyl, 2-chloro-2-propenyloxycarbonyl, 3-methoxycarbonyl-2-propenyloxycarbonyl, 2-methyl-2-propenyloxycarbonyl, 2-butenyloxycarbonyl, cinnamyloxycarbonyl, benzyloxycarbonyl, p-methoxybenzyloxycarbonyl, o-nitrobenzyl-oxycarbonyl and p-nitrobenzyloxycarbonyl; R$^3$ represents hydrogen or a protecting group of the carboxyl group selected from the group consisting of methyl, ethyl, isopropyl, t-butyl, 2-iodoethyl, 2,2,2-trichloroethyl, methoxymethyl, ethoxymethyl, isobutoxymethyl, butyrloxymethyl, pivaloyloxy-methyl, 1-methoxycarbonyloxyethyl, 1-ethoxycarbonyloxyethyl, benzyl, p-methoxybenzyl, o-nitrobenzyl, p-nitrobenzyl, benzhydryl and phthalidyl; R$^4$ represents hydrogen, lower alkyl or a protecting group of the amino group selected from the group consisting of formyl, acetyl, chloroacetyl, dichloroacetyl, propionyl, phenylacetyl, phenoxyacetyl, thienylacetyl, benzyloxycarbonyl, t-butoxy carbonyl, p-nitrobenzyloxycarbonyl, 2,2,2-trichloroethyl, trityl, p-methoxybenzyl, p-nitrobenzyl, diphenylmethyl, pivaloyloxymethyl, trimethylsilyl, t-butyl dimethylsilyl, benzylidene, salicylidene, p-nitrobenzylidene, m-chlorobenzylidene, 3,5-di(t-butyl)-4-hydroxybenzylidene and 3,5-di(t-butyl)benzylidene; R$^6$ represents: (1) hydrogen, (2) lower alkyl, optionally substituted by an optionally protected hydroxy, a carbamoyl, formimidoyl, acetimimidoyl or

wherein R$^7$ and R$^8$ are the same or different and each represents hydrogen, lower alkyl, or a protecting group of the amino group, or (3) a protecting group of the amino group or a protecting group of the imino group; and m is 0 or 1, wherein the hydroxy is protected by the hydroxyl protecting group described above and the amino and imino group are protected by the amino protecting group described above.

2. A carbapenem compound represented by the following formula (II), or a salt thereof:

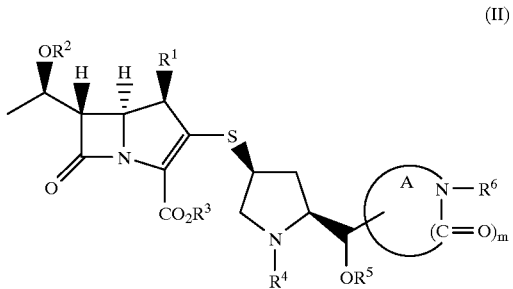

(II)

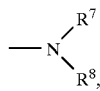

wherein the ring A represents a 3- to 7-membered saturated or partially unsaturated heterocycle containing only nitrogen as heteroatoms and optionally having a ring substituent other than $R^6$ and selected from the group consisting of a hydrogen atom, hydroxyl, mercapto, halogen, cyano, azido, alkyl, alkenyl, alkynyl, alkoxy, halogenoalkyl, guanidino, formimidoyl, acetimidoyl, carbamoyl, thiocarbamoyl, carbamoylalkyl, carbamido, alkanoyl, amino, alkylamino, dialkylamino, aminoalkyl, carboxy, alkoxycarbonyl, alkoxycarbonylalkyl, aminoalkylaminoalkyl, alkylcarbonyloxy, cycloalkyl, cycloalkenyl, phenyl, alkylthio, phenylthio, benzyl, benzoyl and halogenoaryl; $R^1$ represents hydrogen or methyl; $R^2$ and $R^5$ are the same or different and each represents hydrogen or a protecting group of the hydroxyl group selected from the group consisting of trimethylsilyl, t-butyl dimethylsilyl, methoxymethyl, 2-methoxyethoxymethyl, tetrahydropyranyl, benzyl, p-methoxybenzyl, 2,4-dimethoxybenzyl, o-nitrobenzyl, p-nitrobenzyl, trityl, formyl, acetyl, t-butoxycarbonyl, 2-iodoethoxycarbonyl, 2,2,2-trichloroethoxycarbonyl, 2-propenyloxycarbonyl, 2-chloro-2-propenyloxycarbonyl, 3-methoxycarbonyl-2-propenyloxycarbonyl, 2-methyl-2-propenyloxycarbonyl, 2-butenyloxycarbonyl, cinnamyloxycarbonyl, benzyloxycarbonyl, p-methoxybenzyloxycarbonyl, o-nitrobenzyloxycarbonyl and p-nitrobenzyloxycarbonyl; $R^3$ represents hydrogen or a protecting group of the carboxyl group selected from the group consisting of methyl, ethyl, isopropyl, t-butyl, 2-iodoethyl, 2,2,2-trichloroethyl, methoxymethyl, ethoxymethyl, isobutoxymethyl, butyrloxymethyl, pivaloyloxy-methyl, 1-methoxycarbonyloxyethyl, 1-ethoxycarbonyloxyethyl, benzyl, p-methoxybenzyl, o-nitrobenzyl, p-nitrobenzyl, benzhydryl and phthalidyl; $R^4$ represents hydrogen, lower alkyl or a protecting group of the amino group selected from the group consisting of formyl, acetyl, chloroacetyl, dichloroacetyl, propionyl, phenylacetyl, phenoxyacetyl, thienylacetyl, benzyloxycarbonyl, t-butoxy carbonyl, p-nitrobenzyloxycarbonyl, 2,2,2-trichloroethyl, trityl, p-methoxybenzyl, p-nitrobenzyl, diphenylmethyl, pivaloyloxy-methyl, trimethylsilyl, t-butyl dimethylsilyl, benzylidene, salicylidene, p-nitrobenzylidene, m-chlorobenzylidene, 3,5-di(t-butyl)-4-hydroxybenzylidene and 3,5-di(t-butyl)benzylidene; $R^6$ represents: (1) hydrogen, (2) lower alkyl, optionally substituted by an optionally protected hydroxy, a carbamoyl, formimidoyl, acetimimidoyl or wherein $R^7$ and $R^8$ are the same or different and each represents hydrogen, lower alkyl, or a protecting group of the amino group, or (3) a protecting group of the amino group or a protecting group of the imino group; and m is 0 or 1, wherein the hydroxy is protected by the hydroxyl protecting group described above and the amino and imino group are protected by the amino protecting group described above.

3. A compound as claimed in claim 1, or a salt thereof, wherein $R^1$ is methyl, $R^2$, $R^3$, $R^4$, $R^5$ and $R^6$ are each hydrogen and m is 0.

4. A compound as claimed in claim 1, or a salt thereof, wherein $R^1$ is methyl, $R^2$, $R^3$, $R^4$, $R^5$ and $R^6$ are each hydrogen and m is 1.

5. The compound represented by the following formula, or a salt thereof:

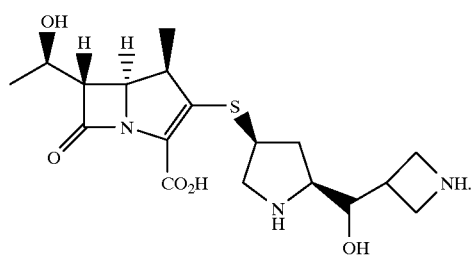

6. The compound represented by the following formula, or a salt thereof:

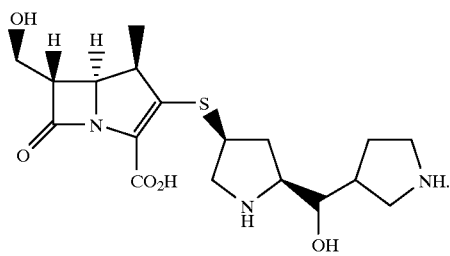

7. The compound represented by the following formula, or a salt thereof:

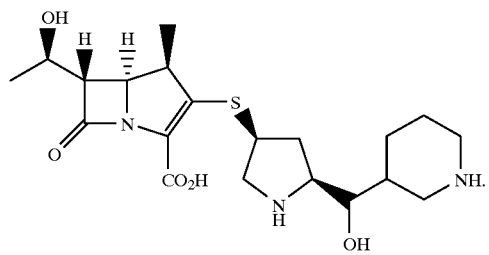

8. The compound represented by the following formula, or a salt thereof:

9. A process for producing a compound as claimed in claim 1, or a salt thereof, which comprises reacting a compound represented by the following formula (III) or a reactive derivative thereof:

(III)

wherein $R^1$ represents hydrogen or methyl; $R^2$ represents hydrogen or the protecting group of the hydroxyl group; and $R^3$ represents hydrogen or the protecting group of the carboxyl group, with a mercaptan represented by the following general formula (IV):

(IV)

wherein the ring A represents a 3- to 7-membered saturated or partially unsaturated heterocycle containing only nitrogen as heteroatoms and optionally having a ring substituent other than $R^6$ and selected from the group consisting of a hydrogen atom, hydroxyl, mercapto, halogen, cyano, azido, alkyl, alkenyl, alkynyl, alkoxy, halogenoalkyl, guanidino, formimidoyl, acetimidoyl, carbamoyl, thiocarbamoyl, carbamoylalkyl, carbamido, alkanoyl, amino, alkylamino, dialkylamino, aminoalkyl, carboxy, alkoxycarbonyl, alkoxycarbonylalkyl, aminoalkylaminoalkyl, alkylcarbonyloxy, cycloalkyl, cycloalkenyl, phenyl, alkylthio, phenylthio, benzyl, benzoyl and halogenoaryl; $R^4$ represents hydrogen, lower alkyl or the protecting group of the amino group; $R^5$ represents hydrogen or the protecting group of the hydroxyl group; $R^6$ represents: (1) hydrogen, (2) lower alkyl, optionally substituted by the optionally protected hydroxy, the carbamoyl, formimidoyl, acetimidoyl or $$-N\begin{matrix}R^7\\R^8,\end{matrix}$$

wherein $R^7$ and $R^8$ are the same or different and each represents hydrogen, lower alkyl, or the protecting group of the amino group, or (3) the protecting group of the amino group or the protecting group of the imino group; and m is 0 or 1, optionally followed by the deblocking reaction.

10. A compound as claimed in claim 1, wherein the ring A is selected from the group consisting of aziridine, azetidine, pyrrolidine, piperidine, homopiperidine, imidazolidine, pyrazolidine, piperazine, pyrroline, imidazoline and pyrazoline.

11. In a method for preventing or treating an illness caused by a bacteria, the improvement comprising administering a pharmacologically efficacious dose of a compound as claimed in claim 1, or a salt thereof, to a patient.

12. A compound as claimed in claim 2 or a salt thereof, wherein $R^1$ is methyl, $R^2$, $R^3$, $R^4$, $R^5$ and $R^6$ are each hydrogen and m is 1.

13. A medicinal composition which comprises a pharmacologically efficacious amount of a compound as claimed in claim 1, or a salt thereof, and pharmacologically acceptable carrier(s).

14. A compound as claimed in claim 2 or a salt thereof, wherein $R^1$ is methyl, $R^2$, $R^3$, $R^4$, $R^5$ and $R^6$ are each hydrogen and m is 0.

* * * * *

UNITED STATES PATENT AND TRADEMARK OFFICE
CERTIFICATE OF CORRECTION

PATENT NO.    : 6,037,341
DATED         : March 14, 2000
INVENTOR(S)   : Nobuaki Sato et al.

It is certified that error appears in the above-identified patent and that said Letters Patent is hereby corrected as shown below:

<u>Title page,</u>
Item [86], please amend PCT No. as follows: change "PCT/JP95/01233" to -- PCT/JP95/01299 --.

<u>Column 37,</u>
Line 52, please replace Formula (I) as follows:

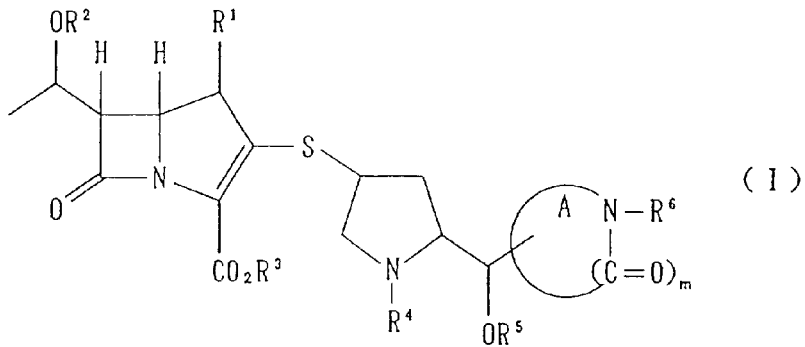

Signed and Sealed this

Twenty-fifth Day of February, 2003

JAMES E. ROGAN
*Director of the United States Patent and Trademark Office*